US010768253B2

(12) United States Patent
Feiweier

(10) Patent No.: US 10,768,253 B2
(45) Date of Patent: Sep. 8, 2020

(54) MR IMAGING WITH SIGNAL SUPPRESSION OF A SPIN SERIES

(71) Applicant: Siemens Aktiengesellschaft, Munich (DE)

(72) Inventor: Thorsten Feiweier, Poxdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 271 days.

(21) Appl. No.: 16/002,467

(22) Filed: Jun. 7, 2018

(65) Prior Publication Data

US 2018/0348322 A1   Dec. 6, 2018

Related U.S. Application Data

(62) Division of application No. 14/457,303, filed on Aug. 12, 2014, now Pat. No. 10,024,940.

(51) Int. Cl.
| | | |
|---|---|---|
| *G01R 33/483* | (2006.01) | |
| *A61B 5/055* | (2006.01) | |
| *G01R 33/56* | (2006.01) | |
| *G01R 33/50* | (2006.01) | |
| *G01R 33/54* | (2006.01) | |
| *G01R 33/561* | (2006.01) | |
| *G01R 33/565* | (2006.01) | |

(52) U.S. Cl.
CPC .......... *G01R 33/4833* (2013.01); *A61B 5/055* (2013.01); *G01R 33/50* (2013.01); *G01R 33/543* (2013.01); *G01R 33/561* (2013.01); *G01R 33/5607* (2013.01); *G01R 33/5602* (2013.01); *G01R 33/56527* (2013.01)

(58) Field of Classification Search
CPC ........... G01R 33/4833; G01R 33/5607; G01R 33/50; G01R 33/543; G01R 33/561; A61B 5/055
See application file for complete search history.

(56) References Cited

U.S. PATENT DOCUMENTS

| | | | |
|---|---|---|---|
| 5,208,536 A | | 5/1993 | Cory |
| 6,064,203 A | * | 5/2000 | Bottomley ............. G01R 33/50 |
| | | | 324/307 |
| 8,077,955 B2 | * | 12/2011 | Dannels ............... G01R 33/246 |
| | | | 324/309 |
| 8,154,294 B2 | | 4/2012 | Takizawa et al. |
| | | | (Continued) |

FOREIGN PATENT DOCUMENTS

JP        2012070964 A      4/2012

OTHER PUBLICATIONS

Bydder et al. "MR Imaging: Clinical Use of the Inversion Recovery Sequence" Journal of Computer Assisted Tomography, 9(4); pp. 659-675, (1985).

(Continued)

*Primary Examiner* — Dixomara Vargas
(74) *Attorney, Agent, or Firm* — Schiff Hardin LLP

(57) ABSTRACT

In a magnetic resonance measurement sequence, an inversion pulse is applied that acts on a longitudinal magnetization of a first spin species and a second spin species, for example on a water portion and a fat portion. An excitation pulse is applied after a predetermined time period. At least one manipulation pulse is subsequently applied, respectively with associated gradient pulse.

23 Claims, 13 Drawing Sheets

(56) References Cited

U.S. PATENT DOCUMENTS

| | | | | |
|---|---|---|---|---|
| 8,502,538 | B2* | 8/2013 | Dannels | G01R 33/243 |
| | | | | 324/307 |
| 9,234,953 | B2* | 1/2016 | Labadie | G01R 33/4818 |
| 9,606,208 | B2 | 3/2017 | Paul | |
| 10,024,940 | B2* | 7/2018 | Feiweier | G01R 33/4833 |
| 2007/0167733 | A1 | 7/2007 | Miyoshi | |
| 2010/0164495 | A1 | 7/2010 | Takizawa et al. | |
| 2010/0239142 | A1* | 9/2010 | Dannels | G01R 33/443 |
| | | | | 382/131 |
| 2010/0239151 | A1* | 9/2010 | Dannels | G01R 33/246 |
| | | | | 382/131 |
| 2011/0241668 | A1 | 10/2011 | Beckmann et al. | |
| 2012/0313641 | A1* | 12/2012 | Labadie | G01R 33/5616 |
| | | | | 324/309 |
| 2013/0069650 | A1 | 3/2013 | Abe | |
| 2013/0169275 | A1 | 7/2013 | Li et al. | |
| 2013/0241552 | A1 | 9/2013 | Hirai | |
| 2014/0062478 | A1 | 3/2014 | Paul | |
| 2015/0042336 | A1* | 2/2015 | Feiweier | A61B 5/055 |
| | | | | 324/309 |
| 2016/0216350 | A1 | 7/2016 | Feiweier | |
| 2020/0033432 | A1* | 1/2020 | Blaimer | G01R 33/50 |

OTHER PUBLICATIONS

Meyer et al: "Simultaneous Spatial and Spectral Selective Excitation", Magn Reson MEd, vol. 15, (1990) pp. 287-304.

Haaseet al:; "1H NMR Chemical Shift Selective (CHESS) Imaging", Phys. Med. Biol. 30, (1985), pp. 341-344.

Lauenstein et al.: "Evaluation of Optimized Inversion-Recovery Fat-Suppression Techniques for T2-Weighted Abdominal MR Imaging", Journal of Magnetic Resonance Imaging 27: (2008); pp. 1448-1454.

Ivanov et al., "A Simple Low-SAR Technique for Chemical-Shift Selection with High-Field Spin-Echo Imaging", Magnetic Resonance in Medicine; vol. 64; (2010) pp. 319-326.

Bottomley et.al.: "In vivo Nuclear Magnetic REsonance Chemical Shift Imaging by Selective Irradiation" in: Proc. Nat. Acad. Sci. vol. 81, (1984) pp. 6856-6860.

Thomassonet.al.: "Phase Modulated Binomial RF Pulses for Fast Spectrally Selective Musculoskeletal Imaging", in: Magnetic Resonance in Medicine, vol. 35, (1996), pp. 563-568.

Park et al.: "Gradient Reversal Technique and its Application to chemical-shift-related NMR Imaging", in: Magnetic Resonance in Medicine, vol. 4, (1987) pp. 526-536.

Nagy et al. " Efficient fat suppression by slice-selection gradient reversal in twice-refocused diffusion encoding", Magnetic Resonance in Medicine, vol. 60, (2008) pp. 1256-1260.

Mürtz et al. "Diffusion-Weighted Whole-Body Mri With Background Body Signal Spression: Technical Improvements at 3.0 T"; Journal of Magnetic Resonance Imaging; vol. 35; (2012) pp. 456-461.

* cited by examiner

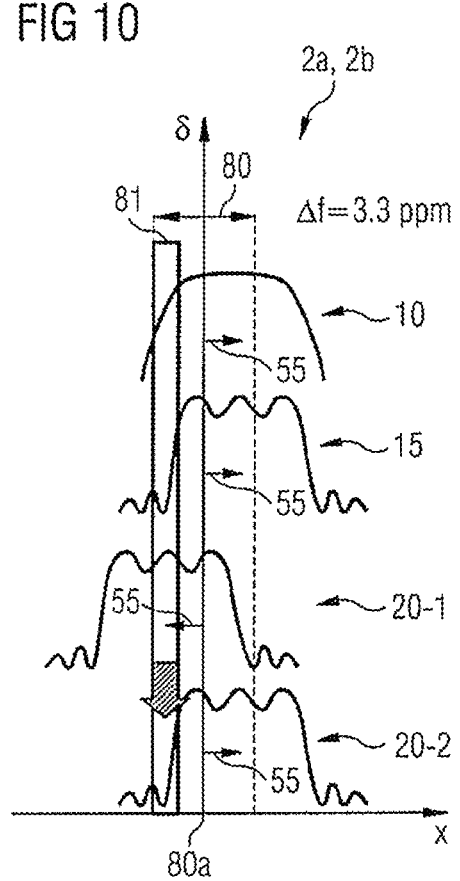

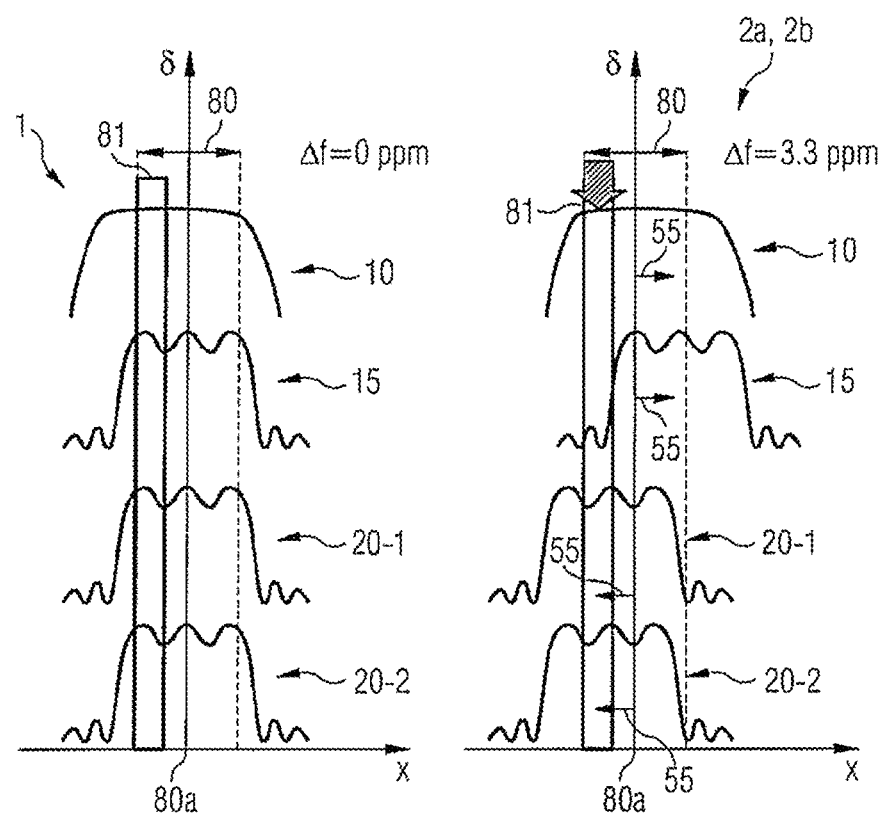

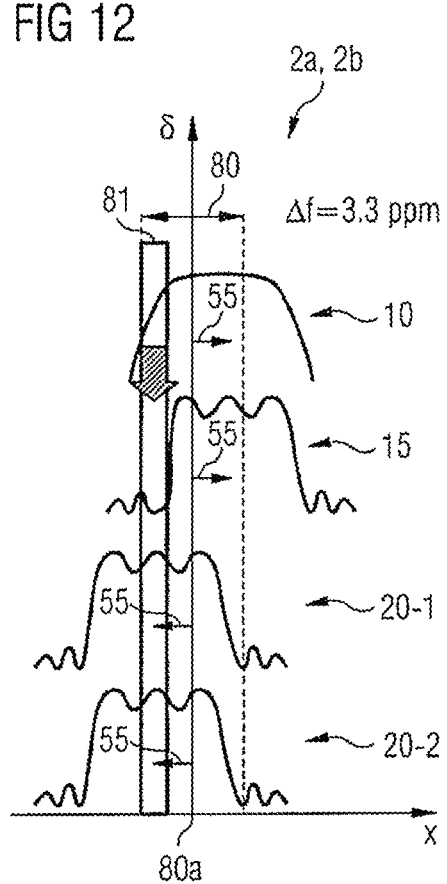

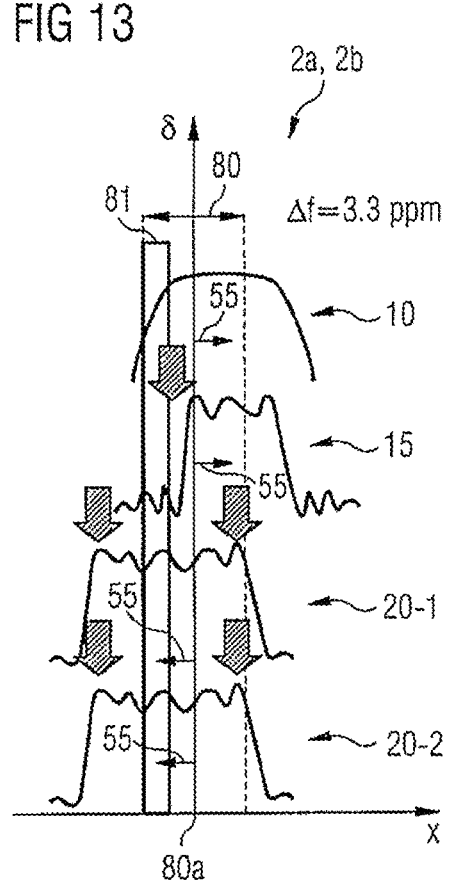

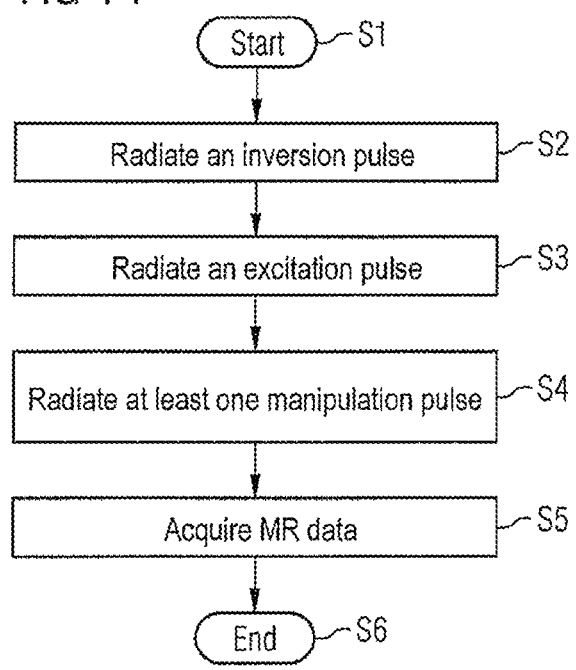

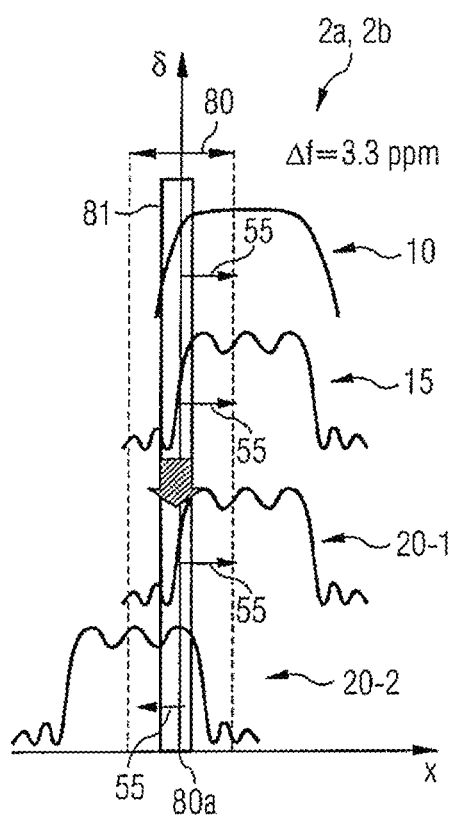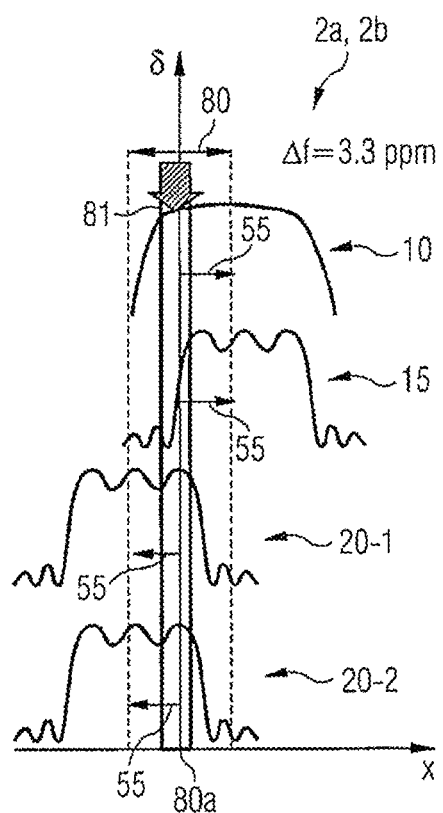

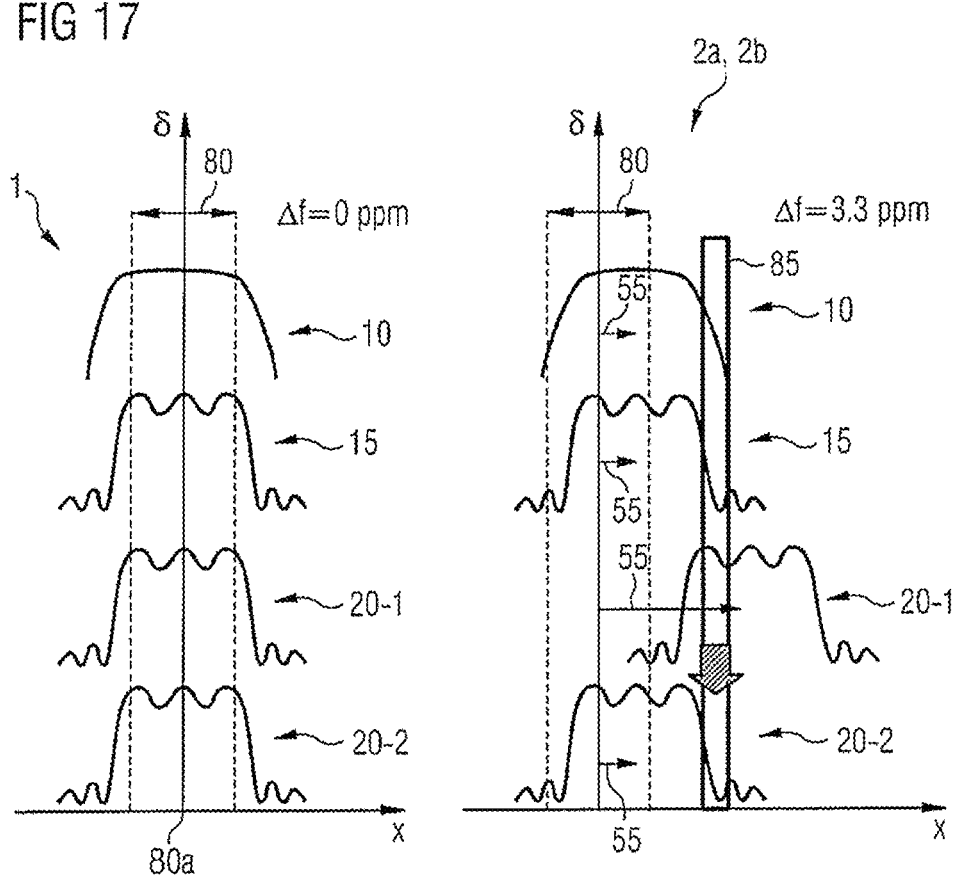

MR IMAGING WITH SIGNAL SUPPRESSION OF A SPIN SERIES

RELATED APPLICATION

The present application is a divisional application of Ser. No. 14/457,303, filed on Aug. 12, 2014, the contents of which are incorporated herein by reference.

BACKGROUND OF THE INVENTION

Field of the Invention

The present invention concerns a method to acquire magnetic resonance data of a first spin species and a magnetic resonance system, and in particular concerns the suppression of a signal of a second spin species in the magnetic resonance data.

Description of the Prior Art

Within the scope of magnetic resonance (MR) data acquisition of signals elicited from nuclear spins, a longitudinal magnetization is polarized in a basic magnetic field. The longitudinal magnetization is excited by an excitation pulse so that a transverse magnetization arises. This can be specifically manipulated, for example dephased and rephased so that an echo is produced. This echo can be detected as a signal in order to provide MR data. Signals from proton nuclear spins are often measured. A spatial resolution of the MR data can be generated by application of gradient pulses that produce spatially variable gradient fields.

Within the scope of the MR measurements (data acquisitions), it is possible to separate spectral components in the MR data, and thus to suppress individual components. The spectral components can original from different spin species. Such techniques often utilize the effect that the resonance frequency of nuclear spins depends on the molecular or chemical environment. This effect is designated as a chemical shift or frequency shift. Different spin species therefore have different resonance frequencies from which the measured spectrum of the MR data is composed. For example, the difference between two resonance frequencies of different spectral portions—i.e. the frequency shift—can be expressed in ppm ("parts per million", i.e. 10-6 [sic]).

The frequency shift between proton nuclear spins in water (water signal) as a first spectral component and proton nuclear spins in fatty acid chains (fat signal) as a second spectral component is often considered. In such a case, a water MR image and/or a fat MR image—i.e. individual MR images of the two spectral components—can be determined using MR data.

For example, a water MR image in which the fat signal is suppressed can be of interest. This is of interest for a variety of clinical and/or medical applications, for example. For example, certain anatomical details or pathologies are shown in a particular manner given suppression of the fat signal, which can be essential to the assessment of the images by a radiologist. In MR spectroscopy, interesting signals (spectral lines) of specific metabolites (i.e. chemical bonds in which the resonance frequency of the protons is characteristically shifted) can be overlapped by the dominating fat signal, and thus cannot be interpreted, or can be interpreted only with difficulty. Moreover, in specific imaging methods, fat signals lead to artifacts that hinder the diagnosis. This applies in particular to echoplanar imaging, in which the fat tissue is often shown shifted by several pixels due to the frequency shift of the fat signal and the small bandwidth along the phase coding direction.

Various techniques for suppression of the fat signal, of the signal originating from the second spin species, in general are known that are based on the frequency shift. One example is the Dixon technique; see W. T. Dixon, "Simple proton spectroscopic imaging" in Radiology 153 (1984) 189-194. An additional technique is the slice selective gradient reversal technique (SSGR); see for example H. W. Park et al., "Gradient Reversal Technique an Application to Chemical-Shift-Related NMR Imaging" in Magn. Reson. Med. 4 (1987) 526-536. In the SSGR technique, use is made of the fact that, in the case of successive radio-frequency (RF) pulses that are respectively accompanied by slice selection gradient pulses with different polarity, spatial domain profiles of a flip angle of the RF pulses do not overlap (or overlap only in part) along a slice selection direction for the spin species to be suppressed. Corresponding techniques are also known, for example from M. Ivanov et al., "A simple low-SAR technique for chemical-shift selection with high-field spin-echo imaging" in Magn. Reson. Med. 64 (2010) 319-326, and Z. Nagy and N. Weiskopf, "Efficient fat suppression by slice-selection gradient reversal in twice-refocused diffusion encoding" in Magn. Reson. Med. 60 (2008) 1256-1260.

Furthermore, it is known that different spin species can have different spin-lattice relaxation times (often also called T1 relaxation time). For example, this is the case for the water signal and the fat signal. One technique that utilizes this effect of different spin-lattice relaxation times in order to suppress the fat portion is short tau inversion generation (short tau inversion recovery, STIR); see for example G. M. Bydder and I. R. Young, "MR Imaging: Clinical Use of the Inversion Recovery Sequence" in J. Comput. Assist. Tomogr. 9 (1985) 659. In the STIR technique, use is made of the fact that a previously inverted longitudinal magnetization of the spin species to be suppressed has a zero crossing at the point in time of an excitation pulse. The time period after which the excitation pulse follows the inversion pulse is often designated as an inversion time, and coincides with the spin-lattice relaxation time of the spin species to be suppressed.

Various methods for selective imaging of one or more spin species are thus known that are based either on the frequency shift or on the different T1 relaxation times. However, such techniques have diverse disadvantages and limitations. The STIR technique can require relatively long preparation times, which can increase the measurement duration. The signal-to-noise ratio of the STIR technique is typically low. The SSGR technique can have a high sensitivity with regard to spatial inhomogeneities of the basic magnetic field, for example because comparably small amplitudes of slice selection gradient pulses and/or low bandwidths of the RF pulses are selected. Moreover, an application of the SSGR technique is often limited to spin echo imaging.

It is also possible that the separation of the spin species does not take place completely, for example a residual signal of the fat component may still be visible in a water MR image. This can limit the clinical evaluation capability. A residual fat signal at the edges of an examination subject also can occur due to inhomogeneities of the basic magnetic field. This can also limit the evaluation capability of corresponding MR images.

In order to remedy such disadvantages, techniques are known that combine the STIR technique, with a partial SSGR technique often being used. "Partial" typically means that no complete suppression of a spin species to be suppressed (for instance the fat component) is achieved solely due to the SSGR portion of the combined STIR-SSGR technique. A more comprehensive suppression of the spin species to be suppressed is typically achieved only in cooperation with the STIR technique. This can make it possible to choose the amplitudes of the slice selection gradient fields to be larger so that the sensitivity to inhomogeneities of the basic magnetic field can be reduced, whereby artifacts in the MR data can be reduced in turn.

However, such combined STIR-SSGR techniques have the disadvantage that suppression of the spin species to be suppressed is often incomplete.

SUMMARY OF THE INVENTION

A need therefore exists for improved techniques of spin species-selective MR imaging. In particular, a need exists for such techniques that enable a particularly good suppression of a spin species to be suppressed (for example fat) within the scope of a STIR-SSGR technique. A need also exists for techniques which enable a comparably low sensitivity relative to inhomogeneities of the basic magnetic field.

According to one aspect of the invention, a method is provided to acquire MR data of a first spin species in a slice of an examination subject, wherein the MR data include a signal of the first spin species. A signal of a second spin species is suppressed in the MR data. The first spin species and the second spin species have a frequency shift relative to one another. The first spin species and the second spin species also have different spin-lattice relaxation times. The method includes the application of an inversion pulse that acts on a longitudinal magnetization of the first spin species in the slice and on a longitudinal magnetization of the second spin species. After a predetermined time period that coincides with the spin-lattice relaxation time of the second species, the method furthermore includes: application of an excitation pulse with an associated first gradient pulse that generates a transverse magnetization. The method furthermore includes the application of at least one manipulation pulse, respectively with an associated second gradient pulse to generate at least one echo of the transverse magnetization of at least the first spin species. The amplitude of the at least one second gradient pulse is different from the amplitude of the first gradient pulse. The method furthermore includes the acquisition of MR data in the entire slice. In a partial region of the slice in which the inversion pulse has different flip angles for the first spin species and the second spin species due to the frequency shift, manipulation pulse has a smaller flip angle for the second spin species than for the first spin species.

For example, in a central region of the slice the inversion pulse can have comparable flip angles for the first spin species and for the second spin species. In the central region of the slice, the excitation pulse for the first spin species and for the second spin species can have comparable flip angles. In the central region of the slice, the at least one manipulation pulse for the first spin species and for the second spin species can have comparable flip angles. For example, the partial region can adjoin the central region. For example, the partial region can reach to an edge of the slice, but it is also possible for the partial region to be arranged within the slice, at a distance from the edges of the slice.

For the second spin spices, the spatial domain profile of the flip angle of the at least one manipulation pulse at least partially overlap with the spatial domain profile of the flip angle of the excitation pulse. Alternatively or additionally, for the second spin species it is also possible for the spatial domain profile of the flip angle of the at least one manipulation pulse to at least partially overlap with the spatial domain profile of the flip angle of the inversion pulse. In general, the case of a partial SSGR component can be present, thus a partial overlap of the frequency-shifted spin species in spite of a frequency shift. An overlap region of two spatial domain profiles can be that region of the spatial domain profiles in which both spatial domain profiles have a finite flip angle>0°.

The slice can designate that spatial region for which the MR data with regard to the first spin species are acquired. In other words, the slice can thus be defined with regard to the first spin species. The slice can also be designated as an imaging slice. Due to the frequency shift between the first spin species and second spin species, the spatial region from which the MR data for the second spin species (if also suppressed) can be acquired can be offset relative to the slice. The slice can have a lateral dimension that is significantly larger than a slice thickness. For example, the slice can be spatially coded by means of the first gradient pulse, which then is what is known as a slice selection gradient pulse. The slice thickness can extend along a slice selection direction. The gradient pulse—or gradient for short—can generate a gradient field which codes the spatial resolution locally via the resonance condition of the nuclear spins.

The fact that the signal of the second spin species is suppressed in the MR data can mean: for comparable portions of the first spin species and second spin species in an image point of the MR data, the signal of the first spin species in the image point is significantly greater than the signal of the second spin species.

For example, the first spin species can be proton nuclear spins in an aqueous environment (water portion). For example, a water MR image can furthermore be provided. For example, the second spin species can be proton nuclear spins in a fat environment (fat portion). The fat portion can include multiple differentiable resonance frequencies, namely due to the multispectral nature of fat. The first spin species could also designate the fat portion and the second spin species the water portion. It is also possible that the first and second spin species do not pertain to the water portion and the fat portion, but rather to silicone and so forth, for example.

The frequency shift can designate a difference between the resonance frequencies of the first and second spin species. The spin-lattice relaxation time can designate a relaxation of the inverted longitudinal magnetization, i.e. typically along a basic magnetic field of the MR system without transversal component. The spin-lattice relaxation time is typically to be delimited relative to a spin-spin relaxation time (often also designated as a T2 relaxation time). The spin-spin relaxation time can be characteristic of a relaxation of the transverse magnetization.

The inversion pulse, the excitation pulse and the manipulation pulse can be RF pulses, for example include an amplitude-modulated microwave signal, for example in a frequency range of kHz to a few GHz. A phase modulation and/or a frequency modulation would also be possible. The inversion pulse can deflect the longitudinal magnetization out of the steady state, typically along the basic magnetic field, such that this is oriented antiparallel to the basic magnetic field. This can in turn mean that the inversion pulse generates no (or no significant) transverse magnetization. The inversion pulse is also often designated as a 180° pulse or reversal pulse.

The predetermined time period can also be designated as an inversion time or TI time. For example, the inversion time can be selected such that the second spin species has a zero crossing of the longitudinal magnetization at a point in time of the application of the excitation pulse; this can in particular be the case when the second spin species has no (or no significant) multispectral spin species. However, it would also be possible for the predetermined time period to be that time period after which amplitudes of all spectral components of the longitudinal magnetization of the second spin species (which can have multispectral portions, for example) add to a minimum value, preferably zero. This can in particular be the case given opposite polarities of the longitudinal magnetization of the spectral components of the second spin species at the point in time of the excitation. For example, the latter can be relevant for the fat component.

For example, the echo can be a spin echo or a stimulated echo. For example, the manipulation pulse can form the echo. For example, the manipulation pulse can be selected from the following group: refocusing pulse, storage pulse and/or restoration pulse. The storage pulse and the restoration pulse can be relevant in cooperation with the stimulated echo: the storage pulse stores a portion of the transversal dephasing state in the form of longitudinal magnetization, and the restoration pulse converts this into a transversal dephasing state again after a predetermined time, which transversal dephasing state rephases as a result and leads to an echo signal. After a dephasing of the transverse magnetization, the refocusing pulse can introduce a dephasing so that the spin echo is formed after a defined time period. A new dephasing following this can be rephased again by an additional refocusing pulse so that a sequence of spin echoes can be generated. It is thereby unnecessary for each echo signal to be actually read out, since only some of the echoes can include the desired contrast information depending on the order of the gradient pulses.

For example, the amplitude of the at least one second gradient pulse and the amplitude of the first gradient pulse can have different polarity, i.e. be oriented along opposite directions. In such a case, it may can occur that, in the central region of the slice, the flip angles of the inversion pulse, of the excitation pulse, and of the at least one manipulation pulse, are comparable. However, it would also be possible for the amplitudes merely to assume different values given the same polarity. Namely, a relative difference of the amplitudes can typically be relevant. The amplitude of the gradient pulse can establish a strength of the change of the gradient field across the location.

In principle, a difference between the flip angles for the different spin species in the partial region of the slice can be ascribed to the frequency shift between the first and second spin species. For example, within the scope of the slice selection via gradient pulses the frequency shift can also produce a spatial of image points. For simplicity, this spatial shift of image points is also designated in the following as a frequency shift. The direction of the frequency shift typically correlates with a polarity of the slice selection gradient pulses that are applied simultaneously with the RF pulses.

For example, the slice can comprise the partial region and the central region. The partial region can thus directly follow the central region along the slice selection direction. However, it would be possible (but not necessary) for the partial region to extend to the edge of the slice. An additional partial region can be present in the other direction along the slice selection direction, but this does not need to be the case.

It is possible that in the partial region the inversion pulse has finite flip angles>0° for the first spin species and/or for the second spin species. For example, it is alternatively or additionally possible for the excitation pulse in the partial region for the second spin species to have a finite flip angle>0°. For example, in the partial region the flip angle of the inversion pulse can be smaller for the second spin species than for the first species. For example, this can be the case because a spatial domain profile of the flip angle of the inversion pulse for the second spin species in the partial region has a falling edge. For example, the flip angle for the first spin species can amount to approximately 180°, for example >170° or preferably >179°. In other words, this can mean that the longitudinal magnetization of the first spin species is essentially completely inverted by the inversion pulse. The flip angle for the second species can accordingly be <170°, for example. In other words, this means that the entire second spin species is not precisely inverted by the inversion pulse. This can have the effect that a residual longitudinal magnetization of the second spin species after the inversion time (residual magnetization) remains even after application of the inversion pulse. In particular, it is possible that this residual magnetization is excited by the excitation pulse to transverse magnetization of the second spin species—and thus can potentially contribute to the MR data as residual signal of the second spin species.

With the techniques described above, it can be achieved that the MR data within the slice have essentially only one signal of the first spin species, and no signal (or no significant signal) of the second spin species. This can be the case because, in the partial region, at least one manipulation pulses for the second spin species has a relatively small flip angle, in spite of the possibly incomplete inversion of the second spin species in the partial region by the inversion pulse due to the residual magnetization. For example, this flip angle can be smaller than 170°, preferably smaller than 120°, particularly preferably smaller than 80°. It would also be possible that at least one of the manipulation pulses for the second spin species has a disappearing flip angle in the partial region.

For example, it would be possible for a first and second manipulation pulse to be respectively applied with associated second gradient pulse. An amplitude of the second gradient pulse of the first manipulation pulse and an amplitude of the second gradient pulse of the second manipulation pulse can be different. The application of two manipulation pulses can in particular be worthwhile within the framework of diffusion coding.

For example, it is possible for the polarity of the amplitude of the second gradient pulse of the first manipulation pulse and the polarity of the amplitude of the second gradient pulse of the second manipulation pulse to be different.

By the use of the different amplitudes of the gradient pulses that belong to the first and second manipulation pulses, it can be achieved that the first and second manipulation pulses act on different (though identical) spatial regions with regard to the second (first) spin species due to the frequency shift. For example, it is possible for an overlap to exist between the spatial regions in which the first and second manipulation pulses act on the second spin species, for example as is the case within the scope of the partial SSGR technique; it would also be possible that no overlap exists.

A special adaptation of the pulse shape of the at least one manipulation pulse may not be necessary. It may not be necessary to pose particularly high requirements for an amplitude of the at least one manipulation pulse so that a microwave exposure of an examined person can be limited. The duration of the at least one manipulation pulse can also turn out to be not particularly long, such that an echo time at which the echo for acquisition of the MR data is formed by each of the at least one manipulation pulses can be comparably short; a signal-to-noise ratio can therefore be increased.

For example, a spatial domain profile of the flip angle of the first manipulation pulse in the partial region can have an edge with a decreasing flip angle. It is also possible for the spatial domain profile of the flip angle of the second manipulation pulse in the partial region to not have an edge with a decreasing flip angle. Alternatively or additionally, the slice thicknesses in which the first and second manipulation pulse refocus the transverse magnetization with a finite flip angle can essentially be identical. For example, the second manipulation pulse in the partial region can have a plateau with an essentially constant flip angle.

The edge can designate a region along the spatial domain profile of the flip angle (for example along the slice selection direction) within which the flip angle exhibits a strong variation across the location. In other words: the edge can designate the region of the change of the amplitude, for example in the case of a trapezoidal spatial domain profile; the edge is typically to be demarcated relative to a plateau of the gradient pulse.

It would also be possible for the first manipulation pulse (second manipulation pulse) to have a disappearing flip angle in the partial region. A disappearing flip angle means: flip angle smaller than 20°, preferably smaller than 10°, particularly preferably smaller than 5°.

In the preceding, techniques have been explained that enable the signal of the second spin species to be suppressed, in particular in the partial region, using the maintenance of a comparably small flip angle of at least one manipulation pulse for the second spin species. In particular, this can be achieved by the excited transverse magnetization of the second spin species being relatively small in the partial region, for example because a majority of the magnetization of the second spin species is inverted by the inversion pulse in the partial region, and therefore is not excited by the excitation pulse radiated at the inversion time. This relatively small fraction of the excited transverse magnetization of the second spin species is further reduced by, in the partial region, only a relatively small amplitude of at least one manipulation pulse acting on the transverse magnetization of the second spin species. The combination of the inversion pulse acting only partially on the second spin species, and the at least one manipulation pulse, resulting in the signal of the second spin species in the slice being suppressed. This forms the basis of the insight that the residual signal of the second spin species originates primarily from the partial region of the slice where the residual magnetization is present.

The invention furthermore concerns a method to acquire MR data of a first spin species in a slice of an examination subject. The MR data include a signal of the first spin species. A signal of a second spin species is suppressed in the MR data. The first spin species and the second spin species have a frequency shift relative to one another. The first spin species and the second spin species also have different spin-lattice relaxation times. The method includes the application of an inversion pulse that acts on a longitudinal magnetization of the first spin species and the second spin species in the slice. After a predetermined time period, which coincides with the spin-lattice relaxation time of the second spin species, the method furthermore includes: apply an excitation pulse with an associated first gradient pulse that generates a transverse magnetization. The method furthermore includes the application of at least one manipulation pulse, respectively with an associated second gradient pulse to generate at least one echo of the transverse magnetization of at least the first spin species. The amplitude of the at least one second gradient pulse is different from the amplitude of the first gradient pulse. The method furthermore includes the acquisition of MR data in the entire slice. In a partial region of the slice in which the inversion pulse has different flip angles for the first spin species and the second spin species due to the frequency shift, the excitation pulse for the second spin species has a disappearing flip angle.

A disappearing flip angle means: a flip angle smaller than 20°, preferably smaller than 10°, particularly preferably smaller than 5°. No significant excitation of the residual magnetization of the second spin species thus occurs. Because the excitation pulse in the partial region has a disappearing flip angle for the second spin species, it can be achieved that the residual magnetization of the second spin species that possibly remains in the steady state after the inversion pulse is not excited. The residual signal of the second spin species is reduced. The signal of the second spin species can thereby be suppressed in the MR data.

For example, the excitation pulse can have a trapezoidal spatial domain profile along the slice selection direction. The plateau of the trapezoidal excitation pulse can be limited by edges on both sides. The plateau can define a slice thickness within which the transverse magnetization is generated. For example, it would be possible that the excitation pulse has a comparably small edge width. For example, the edge width can amount to only a small fraction of the width of the plateau, for example only 10% or smaller.

For example, a spatial domain profile of the flip angle of the excitation pulse can have an edge width that is smaller than the edge width of the spatial domain profile of the flip angle of the at least one manipulation pulse.

Such a reduction of the edge width of the excitation pulse causes the excitation pulse in the partial region to have a disappearing flip angle. In this regard, it is possible that a slice thickness in which the excitation pulse excites the transverse magnetization (meaning a width of the plateau of the excitation pulse, for example) to be chosen essentially independently of the edge width.

For example, the excitation pulse can excite the transverse magnetization in a slice thickness with finite flip angle which is smaller than the slice thickness in which the at least one manipulation pulse refocuses the transverse magnetization with finite flip angle.

For example, the excitation pulse can excite the transverse magnetization in a slice thickness with finite flip angle that is approximately the same as the width of the slice.

In other words, it is possible for the plateau of the at least one manipulation pulse to be larger than a plateau of the excitation pulse. Reducing the slice thickness excited by the excitation pulse, causes the excitation pulse to have a disappearing flip angle in the partial region.

For example, the at least one manipulation pulse can refocus the transverse magnetization in a slice thickness with finite flip angle that is larger by a factor of 1.5 (preferably of 2) than the width of the slice.

It can therefore be ensured that a complete refocusing of the transverse magnetization takes place. This can reduce artifacts in the MR data and enables a good agreement of desired imaging slice and the region from which the signal of the first spin species contributes to the MR image.

The invention also concerns a method to acquire MR data of a first spin species in a slice of an examination subject. The MR data include a signal of the first spin species. A signal of a second spin species is suppressed in the MR data. The first spin species and the second spin species have a frequency shift relative to one another. The first spin species and the second spin species also have different spin-lattice relaxation times. The method includes the application of an inversion pulse that acts on a longitudinal magnetization of the first spin species and the second spin species in the slice. After a predetermined time period which coincides with the spin-lattice relaxation time of the second spin species, the method furthermore includes: apply an excitation pulse with an associated first gradient pulse that generates a transverse magnetization. The method furthermore includes the application of at least one manipulation pulse, respectively with an associated second gradient pulse to generate at least one echo of the transverse magnetization of at least the first spin species. The amplitude of the at least one second gradient pulse is different from the amplitude of the first gradient pulse. The method furthermore includes the acquisition of MR data in the entire slice. A spatial domain profile of the flip angle of the inversion pulse is asymmetrical for the first spin species relative to a middle of the slice.

For example, it would be possible for the inversion pulse to have a comparable flip angle for the first spin species and the spin species in the entire slice.

For example, the spatial domain profile of the flip angle of the inversion pulse can have a larger dimension counter to the direction of the frequency shift of the second spin species, relative to the first spin species, than along the direction of the frequency shift of the second spin species, relative to the first spin species.

In such a scenario, no (or no significant) partial region of the slice is thus present in which the inversion pulse has a smaller flip angle for the second spin species than for the first spin species, and thereby simultaneously experiences a significant excitation of transverse magnetization due to the excitation pulse. In other words: in no region in which the inversion pulse for the second spin species has flip angles significantly <180° (thus has an edge or disappearing flip angles) can the excitation pulse also have finite flip angles for the second spin species. When the inversion pulse (in particular also for the second spin species) also excites a sufficiently large slice thickness in the spatial domain, the very predominant portion of all relevant nuclear spins of the second spin species is inverted by the inversion pulse. In particular, the residual magnetization of the second spin species that remains after the inversion pulse can then turn out to be comparably small. However, the inverted part of the second spin species then does not (or does not significantly) contribute to the signal in the MR data because the excitation pulse is radiated after the predetermined time period—thus at a point in time at which the longitudinal component of the inverted portion of the second spin species precisely exhibits a zero crossing. This excitation pulse acts only on the remaining residual magnetization of the second spin species, which however can turn out to be relatively small according to the techniques described in the preceding. For example, the inversion pulse can excite the longitudinal magnetization with the flip angle in a slice thickness that is larger by a factor of 1.5—preferably by a factor of 2—than the slice thickness of the slice.

For such techniques, it can be necessary to use a relatively wide spatial domain profile of the inversion profile along the slice selection direction (slice thickness). This can in principle involve disadvantageous effects. For example, for a relatively wide slice thickness it can be necessary to use relatively small amplitudes of the gradient pulses; this can in turn increase a sensitivity relative to inhomogeneities of the basic magnetic field. This can be the case because the gradient field strength is small in comparison to deviations of the basic magnetic field strength. Furthermore, the maximum amplitude of the inversion pulse is also limited, for instance for reasons of biological compatibility of the microwave exposure involved with the radiation of the inversion pulse. In particular, typical limited limit values of the specific absorption rate (SAR) are not to be exceeded.

Therefore, it can be particularly advantageous if the inversion pulse widens asymmetrically along that direction in which the residual magnetization of the second spin species would otherwise occur due to the frequency shift of the inversion pulse. In particular, the asymmetry can correlate with the strength of the frequency shift. For example, the asymmetry be chosen to be greater (lesser) the larger (smaller) the frequency shift between the two spin species.

In the preceding, techniques were explained for the acquisition of MR data according to different aspects. For example, by means of such techniques the effect of a particularly good suppression of the signal of the second spin species in the MR data can be achieved. Such techniques described in the preceding can also be designated as a STIR-SSGR technique. For example, the combination of inversion pulse and excitation pulse can thus be designated as the STIR portion of the combined STIR-SSGR technique. The combination of excitation pulse with the first gradient pulse and with the at least one manipulation pulse can also be designated as the SSGR portion of the combined STIR-SSGR technique. A complete or a partial SSGR technique can be used depending on how large the difference is chosen to be between the amplitudes of the first and second gradient pulse, i.e. how strong the frequency shift turns out to be a complete (partial) SSGR technique can be present if the spatial domain profiles of the excitation pulse and of the at least one manipulation pulse are completely (partially) separate for the second spin species, i.e. have no (a partial) overlap.

According to one aspect, the invention concerns an MR system to acquire MR data of a first spin species in a slice of an examination subject. The MR data include a signal of the first spin species. In the MR data, a signal of a second spin species is suppressed. The first spin species and the second spin species have a frequency shift relative to one another. The first spin species and the second spin species have different spin-lattice relaxation times. The MR system has a transmission unit and a gradient system that are designed in order to implement the following steps: apply an inversion pulse that acts on a longitudinal magnetization of the first spin species and the second spin species in the slice; after a predetermined time period that coincides with the spin-lattice relaxation time of the second spin species, apply an excitation pulse with an associated first gradient pulse that generates a transverse magnetization; apply at least one manipulation pulse, respectively with an associated second gradient pulse to generate at least one echo of the transverse magnetization of the first spin species, wherein an amplitude of the at least one second gradient pulse is different than an amplitude of the first gradient pulse. The MR system furthermore has a reception unit that is designed in order to acquire MR data in the entire slice. In a partial region of the slice in which the inversion pulse has different flip angles for the first spin species and the second spin species due to the frequency shift, at least one of the at least one manipulation pulses has a smaller flip angle for the second spin species than for the first spin species.

According to this aspect of the invention, the MR system can be designed in order to execute a method to acquire MR data according to a further aspect.

For such an MR system, effects can be achieved that are comparable to the effects that can be achieved for the method to acquire MR data according to a further aspect.

The invention furthermore concerns an MR system to acquire MR data of a first spin species in a slice of an examination subject. The MR data include a signal of the first spin species. In the MR data, a signal of a second spin species is suppressed. The first spin species and the second spin species have a frequency shift relative to one another. The first spin species and the second spin species have different spin-lattice relaxation times. The MR system has a transmission unit and a gradient system that are designed in order to implement the following steps: apply an inversion pulse that acts on a longitudinal magnetization of the first spin species and the second spin species in the slice; after a predetermined time period that coincides with the spin-lattice relaxation time of the second spin species, apply an excitation pulse with an associated first gradient pulse that generates a transverse magnetization; apply at least one manipulation pulse, respectively with an associated second gradient pulse to generate at least one echo of the transverse magnetization of the first spin species, wherein the amplitude of the at least one second gradient pulse is different than the amplitude of the first gradient pulse. The MR system furthermore has a reception unit that is designed in order to acquire MR data in the entire slice. In a partial region of the slice in which the inversion pulse has different flip angles for the first spin species and the second spin species due to the frequency shift, the excitation pulse for the second spin species has a disappearing flip angle.

According to this embodiment, the MR system can be designed in order to execute a method to acquire MR data according to a further aspect.

For such an MR system, effects can be achieved that are comparable to the effects that can be achieved for the method to acquire MR data according to a further aspect.

The invention concerns an MR system to acquire MR data of a first spin species in a slice of an examination subject. The MR data include a signal of the first spin species. In the MR data, a signal of a second spin species is suppressed. The first spin species and the second spin species have a frequency shift relative to one another. The first spin species and the second spin species have different spin-lattice relaxation times. The MR system has a transmission unit and a gradient system that are designed in order to implement the following steps: apply an inversion pulse that acts on a longitudinal magnetization of the first spin species and the second spin species in the slice; after a predetermined time period that coincides with the spin-lattice relaxation time of the second spin species, apply an excitation pulse with an associated first gradient pulse that generates a transverse magnetization; apply at least one manipulation pulse, respectively with an associated second gradient pulse to generate at least one echo of the transverse magnetization of the first spin species, wherein an amplitude of the at least one second gradient pulse is different than an amplitude of the first gradient pulse. The MR system furthermore has a reception unit that is designed in order to acquire MR data in the entire slice. For the first spin species, a spatial domain profile of the flip angle of the inversion pulse is asymmetrical relative to a middle of the slice.

According to the presently discussed aspect, the MR system can be designed in order to execute a method to acquire MR data according to a further aspect.

For such an MR system, effects can be achieved that are comparable to the effects that can be achieved for the method to acquire MR data according to a further aspect.

According to one aspect, the invention concerns a method to acquire MR data of a first spin species in a slice of an examination subject. The MR data include a signal of the first spin species. In the MR data, a signal of a second spin species is suppressed. The first spin species and the second spin species have a frequency shift relative to one another and also have different spin-lattice relaxation times. The method includes the application of an inversion pulse that acts on a longitudinal magnetization of the first spin species in the slice and on a longitudinal magnetization of the second spin species. After a predetermined time period that coincides with the spin-lattice relaxation time of the second spin species, the method furthermore includes: application of an excitation pulse with an associated first gradient pulse that generates a transverse magnetization. The method furthermore includes the application of at least two manipulation pulses, respectively with an associated second gradient pulse to generate at least one echo of the transverse magnetization of at least the first spin species. An amplitude of at least one second gradient pulse is different than an amplitude of the first gradient pulse. The method furthermore includes the acquisition of MR data in the entire slice, wherein at least one of the at least two manipulation pulses and the excitation pulse have a spatial domain profile with an edge in an edge region in which a spatial domain profile of a flip angle of the inversion pulse for the second spin species has an edge or disappearing flip angle and in which the excitation pulse for the second spin species has finite flip angles.

The method according to the presently discussed aspect can be designed corresponding to the method according to further discussed aspects. In particular, diverse properties and effects that have been discussed in the preceding with regard to the partial region can also be applied with regard to the edge region. For example, corresponding characterizing properties (as discussed in the preceding for the partial region) can apply to the edge region insofar as the edge region lies within the slice. For the edge region that lies within the slice, it can thus be the case that within the edge region, the inversion pulse has different flip angles for the first spin species and for the second spin species due to the frequency shift. However, the edge region can also lie at least partially outside of the slice.

By means of the these techniques, it can be achieved that the residual signal of the second spin species is suppressed in that spatial region in which a complete inversion of the second spin species does not occur (and therefore the residual magnetization is deflected by the finite flip angle of the excitation pulse). This is achieved via the double edge of the excitation pulse and of the at least one manipulation pulse.

It is possible that fewer echoes are formed than manipulation pulses, for example if the manipulation pulses are storage and/or restoration pulses. In particular, specific echoes can also have a not-insignificant signal amplitude. It is unnecessary that MR data be acquired for every formed echo. However, it is possible to acquire MR data for every formed echo.

For example, a first and second manipulation pulse can be applied, respectively with associated gradient pulse. An amplitude of the second gradient pulse of the first manipulation pulse and an amplitude of the second gradient pulse of the second manipulation pulse can be different. For example, these amplitudes can have the same polarity. This can therefore produce the effect that the frequency shift for both manipulation pulses is oriented the same, for example relative to a middle point of the slice. In particular, the scenario of a partial SSGR component can be present in which the spatial domain profiles of the flip angle of the RF pulses at least partially overlap.

For example, the amplitude of the at least one second gradient pulse and the amplitude of the first gradient pulse can have different polarities, i.e. be oriented along opposite directions. In particular in such a case, the situation can occur that the flip angles of the inversion pulse, of the excitation pulse and of the at least one manipulation pulse are comparable in the central region of the slice. However, it would also be possible that the amplitudes merely assume different values given the same polarity. Namely, a relative difference of the amplitudes can typically be relevant. The amplitude of the gradient pulse can establish the strength of the change of the gradient field over the location.

According to a further aspect, the invention concerns a method to acquire MR data of a first spin species in a slice of an examination subject. The MR data include a signal of the first spin species. In the MR data, a signal of a second spin species is suppressed. The first spin species and the second spin species have a frequency shift relative to one another and also have different spin-lattice relaxation times. The method includes the application of an inversion pulse that acts on a longitudinal magnetization of the first spin species in the slice and on a longitudinal magnetization of the second spin species. After a predetermined time period that coincides with the spin-lattice relaxation time of the second spin species, the method furthermore includes: application of an excitation pulse with an associated first gradient pulse that generates a transverse magnetization. The method furthermore includes the application of at least one manipulation pulses, respectively with an associated second gradient pulse to generate at least one echo of the transverse magnetization of at least the first spin species. An amplitude of at least one second gradient pulse is different than an amplitude of the first gradient pulse. The method furthermore includes the acquisition of MR data in the entire slice. The excitation pulse for the second spin species has disappearing flip angles in an edge region in which a spatial domain profile of a flip angle of the inversion pulse for the second spin species has an edge or disappearing flip angle.

As described in the preceding with regard to further aspects of the present invention, for this the spatial domain profile of the flip angle of the excitation pulse can have a comparably small slice thickness and/or the spatial domain profile of the flip angle of the excitation pulse can have a comparably sharp edge.

With the method according to the presently discussed aspect, effects can be achieved that are comparable to the effects that can be achieved for further aspects of the present invention.

According to a further aspect, the invention concerns a method to acquire MR data of a first spin species in a slice of an examination subject. The MR data include a signal of the first spin species. In the MR data, a signal of a second spin species is suppressed. The first spin species and the second spin species have a frequency shift relative to one another and also have different spin-lattice relaxation times. The method includes the application of an inversion pulse that acts on a longitudinal magnetization of the first spin species in the slice and on a longitudinal magnetization of the second spin species. After a predetermined time period that coincides with the spin-lattice relaxation time of the second spin species, the method furthermore includes: application of an excitation pulse with an associated first gradient pulse that generates a transverse magnetization. The method furthermore includes the application of at least one manipulation pulses, respectively with an associated second gradient pulse to generate at least one echo of the transverse magnetization of at least the first spin species. An amplitude of at least one second gradient pulse is different than an amplitude of the first gradient pulse. The method furthermore includes the acquisition of MR data in the entire slice. The spatial domain profile of a flip angle of the inversion pulse for the second spin species has a maximized flip angle in a region in which the excitation pulse for the second spin species has finite flip angles, wherein the spatial domain profile of the flip angle of the inversion pulse for the first spin species is asymmetrical relative to a middle of the slice.

For example, the maximized flip angle of the inversion pulse can mean: flip angle>170°, preferably >175°, particularly preferably >179°. For example, the maximized flip angle can mean: essentially the entire longitudinal magnetization of the second spin species is inverted there. For example, the maximized flip angle can mean: no or no significant residual magnetization in this region at the point in time of the excitation.

The finite flip angle of the excitation pulse can mean a flip angle>10° or significant excitation.

In other words: the inversion pulse can thus nearly completely invert the longitudinal magnetization of the second species where the excitation pulse acts on the second spin species. In cooperation with the STIR component, a particularly small residual signal of the second spin species can be achieved.

According to the presently discussed aspect, with the method effects can be achieved that are comparable to the effects that can be achieved for additional aspects of the present invention.

According to a further aspect, the invention concerns an MR system to acquire MR data of a first spin species in a slice of an examination subject. The MR data include a signal of the first spin species. In the MR data, a signal of a second spin species is suppressed. The first spin species and the second spin species have a frequency shift relative to one another and also have different spin-lattice relaxation times. The MR system has a transmission unit and a gradient system that are designed in order to implement the following steps: apply an inversion pulse that acts on a longitudinal magnetization of the first spin species in the slice and on a longitudinal magnetization of the second spin species; after a predetermined time period that coincides with the spin-lattice relaxation time of the second spin species, apply an excitation pulse with an associated first gradient pulse that generates a transverse magnetization; and apply at least two manipulation pulses, respectively with an associated second gradient pulse to generate at least one echo of the transverse magnetization of at least the first spin species. The amplitude of at least one second gradient pulse is different than an amplitude of the first gradient pulse. The MR system furthermore has a reception unit that is designed in order to acquire MR data in the entire slice. At least one of the two manipulation pulses and the excitation pulse has a spatial domain profile of the flip angle with an edge in an edge region in which a spatial domain profile of a flip angle of the inversion pulse for the second spin species has an edge or disappearing flip angle and in which the excitation pulse for the second spin species has finite flip angles.

The MR system according to the presently discussed aspect can be designed in order to execute a method to acquire MR data according to a further aspect.

For such an MR system, effects can be achieved that are comparable to the effects that can be achieved for the method to acquire MR data according to a further aspect.

According to a further aspect, the invention concerns an MR system to acquire MR data of a first spin species in a slice of an examination subject. The MR data include a signal of the first spin species. In the MR data, a signal of a second spin species is suppressed. The first spin species and the second spin species have a frequency shift relative to one another and also have different spin-lattice relaxation times. The MR system has a transmission unit and a gradient system. These are designed in order to implement the following steps: apply an inversion pulse that acts on a longitudinal magnetization of the first spin species in the slice and on a longitudinal magnetization of the second spin species; after a predetermined time period that coincides with the spin-lattice relaxation time of the second spin species, apply an excitation pulse with an associated first gradient pulse that generates a transverse magnetization; and apply at least two manipulation pulses, respectively with an associated second gradient pulse to generate at least one echo of the transverse magnetization of at least the first spin species. An amplitude of the second gradient pulse is different than an amplitude of the first gradient pulse. The MR system furthermore has a reception unit that is designed in order to acquire MR data in the entire slice. The excitation pulse for the second spin species has disappearing flip angles in an edge region in which a spatial domain profile of a flip angle of the inversion pulse for the second spin species has an edge or disappearing flip angle.

The MR system according to the presently discussed aspect can be designed in order to execute a method to acquire MR data according to a further aspect.

For such an MR system, effects can be achieved that are comparable to the effects that can be achieved for the method to acquire MR data according to a further aspect.

According to a further aspect, the invention concerns an MR system to acquire MR data of a first spin species in a slice of an examination subject. The MR data include a signal of the first spin species. In the MR data, a signal of a second spin species is suppressed. The first spin species and the second spin species have a frequency shift relative to one another and also have different spin-lattice relaxation times. The MR system has a transmission unit and a gradient system. These are designed in order to implement the following steps: apply an inversion pulse that acts on a longitudinal magnetization of the first spin species in the slice and on a longitudinal magnetization of the second spin species; after a predetermined time period that coincides with the spin-lattice relaxation time of the second spin species, apply an excitation pulse with an associated first gradient pulse that generates a transverse magnetization; apply at least one manipulation pulse, respectively with an associated second gradient pulse to generate at least one echo of the transverse magnetization of at least the first spin species. An amplitude of the second gradient pulse is different than an amplitude of the first gradient pulse. The MR system furthermore has a reception unit that is designed in order to acquire MR data in the entire slice. In a region in which the excitation pulse for the second spin species has finite flip angles, a spatial domain profile of a flip angle of the inversion pulse has a maximized flip angle. For the first spin species, a spatial domain profile of the flip angle of the inversion pulse is asymmetrical relative to a middle of the slice.

The MR system according to the presently discussed aspect can be designed in order to execute a method to acquire MR data according to a further aspect.

For such an MR system, effects can be achieved that are comparable to the effects that can be achieved for the method to acquire MR data according to a further aspect.

The features presented above and features that are described in the following can be used not only in the corresponding, explicitly presented combinations, but rather also in additional combinations or in isolation, without departing from the scope of the invention. In particular, it is possible to combine the features and properties of the different methods to acquire MR data or, respectively, of the different MR systems with one another.

For example, it is possible to also apply the different techniques and properties (that have been discussed in the preceding with regard to the partial region or, respectively, with regard to aspects that are based on the partial region) to the edge region or, respectively, to aspects that are based on the edge region. In general, the edge region can also extend at least in part outside of the slice. It can also be possible to apply properties and characteristics of the edge region to the partial region.

For example, it would be possible that the methods according to different aspects of the present invention furthermore include: analyze the spatial domain profile of the flip angle of at least the inversion pulse for the first and second spin species, and selectively apply the different techniques according to different aspects depending on the analysis.

BRIEF DESCRIPTION OF THE DRAWINGS

FIG. 10 shows spatial domain profiles of the flip angle for the RF pulses of FIG. 9 along the slice selection direction.

FIG. 11 shows spatial domain profiles of the flip angle for RF pulses according to different embodiments along the slice selection direction for two spin species, wherein an inversion pulse widens asymmetrically.

FIG. 12 shows spatial domain profiles of the flip angle for RF pulses according to different embodiments along the slice selection direction, in which an excitation pulse has a reduced edge width.

FIG. 13 shows spatial domain profiles of the flip angle for RF pulses according to different embodiments along the slice selection direction, in which an excitation pulse has a reduced plateau width.

FIG. 14 is a flowchart of a method according to various embodiments of the invention.

FIG. 15 shows spatial domain profiles of the flip angle for RF pulses according to various embodiments along the slice selection direction.

FIG. 16 shows spatial domain profiles of the flip angle for RF pulses according to various embodiments along the slice selection direction, wherein an inversion pulse is widened asymmetrically.

FIG. 17 shows spatial domain profiles of the flip angle for RF pulses according to various embodiments along the slice selection direction in which two manipulation pulses have different amplitudes with the same polarity.

DESCRIPTION OF THE PREFERRED EMBODIMENTS

Figure 1:
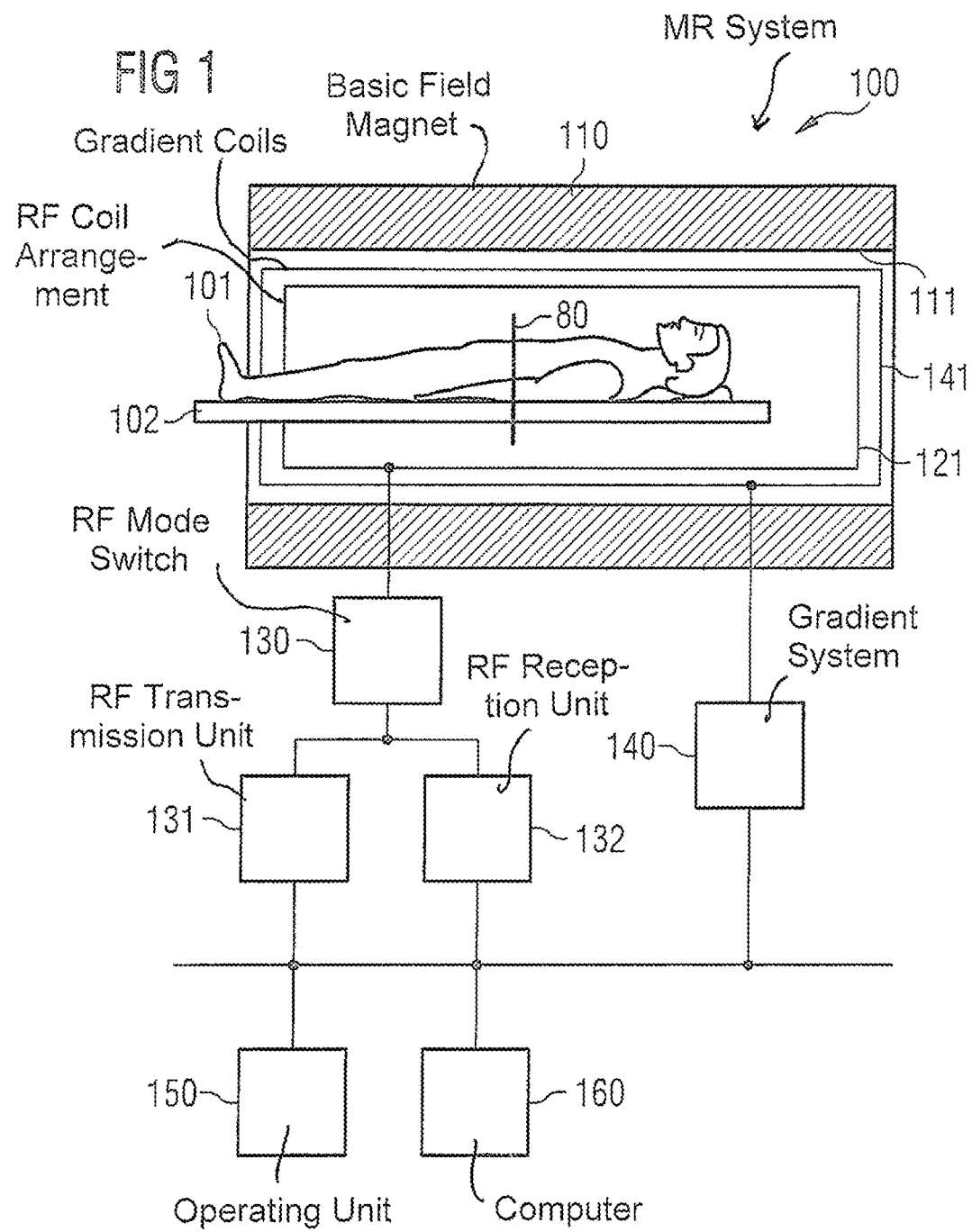
FIG. 1 schematically illustrates an MR system.

In the following, the present invention is explained in detail using preferred embodiments with reference to the drawings. In the figures, identical reference characters designate identical or similar elements. The figures are schematic representations of various embodiments of the invention. Elements shown in the figures are not necessarily represented true to scale. Rather, the different elements shown in the figures are rendered such that their function and general purpose are understandable to those skilled in the art. Connections and couplings that are shown in the figures between functional units and elements can also be implemented as indirect connections or couplings. A connection or coupling can be implemented in a hardwired or wireless manner. Functional units can be implemented as hardware, software or as a combination of hardware and software.

In the following, techniques are described that are used for an MR measurement (data acquisition) of a first spin species given simultaneous suppression of the signal of a second spin species. In particular, those techniques in which an inversion pulse, an excitation pulse and at least one manipulation pulse are used to form at least one echo of the first spin species can be used in connection with STIR-SSGR techniques. In particular, one or more of the manipulation pulses can be accompanied by a slice selection gradient pulse that has a different amplitude than the slice selection gradient pulse of the excitation pulse which forms the SSGR component of the STIR-SSGR technique. After an inversion time, the excitation pulse can be radiated following the inversion pulse, which forms the STIR component of the STIR-SSGR technique.

While it may be sufficient to select only one sufficiently different amplitude, in the following the specific case is discussed wherein the amplitude of the slice selection gradient pulse of the excitation pulse and the amplitude of at least one manipulation pulse have different polarities. It is possible that the magnitude of the amplitudes is the same, given different polarities. This example, however, is not limiting, and corresponding techniques can also be applied for a situation in which the amplitudes do not have respectively different polarities, but rather assume sufficiently different values.

In the following, reference is also made to the at least one manipulation pulse, predominantly as a refocusing pulse. The described techniques can also be used in connection with other manipulation pulses, for example in particular with a storage pulse and/or a restoration pulse.

The invention is based on the insight that a residual signal of a residual magnetization of the second spin species to be suppressed can occur in a partial region of the slice from which the MR data of the first spin species are acquired. In different embodiments, measures are taken that allow this residual magnetization of the second spin species to be more completely suppressed than is the case in other implementations.

In one embodiment, a targeted inversion of only one slice selection gradient pulse can be implemented by at least two refocusing pulses relative to the excitation pulse. For example, if only one of the refocusing pulses is chemically shifted in the counter-direction, only this has nearly ideal refocusing conditions for the residual magnetization of the second spin species in the partial region. The other refocusing pulse in the partial region has only small flip angles (for example <180°), which overall leads to a signal suppression of the second spin species.

An additional measure that can be applied alternatively or additionally is the targeted improvement of the excited spatial domain profile of the excitation pulse. The spatial domain profile typically designates the flip angle as a function of the location along the slice selection direction. For example, the partial region (and thus also the residual signal of the second spin species) can be reduced in that, for example, the transition or the edge between an excitation with predetermined flip angle $\alpha$ and such an excitation with flip angle 0° is implemented more sharply. A sharper slice profile on one side—in particular in the opposite direction of the chemical shift of the seconds relative to the first spin species—can be preferred. A longer RF pulse typically incurs a sharper slice profile. This can lead to an extension of the echo time, which in turn can reduce a signal-to-noise ratio. Therefore, a tradeoff can be made.

An additional measure that can be alternatively or additionally applied is the targeted change of the interaction of excitation pulse and refocusing pulse. It is thus possible to modify the excitation pulse such that excites the desired slice thickness of the slice, and not a slice that is wider by 20%-50%, for example. At the same time, it is possible to adapt the at least one refocusing pulse such that the magnetization from the desired slice still delivers the essential signal contributions in interaction with the excitation pulse. For example, this is achieved by increasing the slice thickness of the slice refocused by the at least one refocusing pulse is increased. The excitation pulse is then typically limited to a region that has been nearly ideally inverted by the preceding inversion pulse, such that the residual signal of the second spin species can be reduced.

An additional measure that can alternatively or additionally be applied is the widening of the slice thickness on which the inversion pulse acts. The residual signal of the second spin species can be reduced by widening of the inversion slice such that all nuclear spins of the second spin species that are detected by the excitation pulse experience a nearly ideal inversion. A widening in the direction opposite the chemical shift is sufficient, which reduces the requirements for the amplitude of the slice selection gradient pulse (and therefore the SAR). For example, the amplitude of the inversion pulse (and SAR) can likewise be reduced by using (for example) adiabatic hyperbolic secant (HSn) pulses (with n>1) or a frequency offset corrected inversion (FOCI) pulse.

All such measures—alone or in combination—allow a suppression of the signal of the second spin species in the MR data. In the following, the first spin species is referred to as a water portion and the second spin species is referred to as a fat portion. However, it is intuitively possible to also apply corresponding techniques to other spin species than water and fat. For example, those techniques described in the preceding for the generation of a water MR image and/or in particular within the scope of a diffusion imaging can be used. Diverse medical applications in the following can therefore be implemented.

In FIG. 1, an MR system 100 is shown that is designed to implement techniques, methods and steps according to the invention. The MR system 100 has a basic field magnet 110 that defines a tube 111. The basic field magnet 110 generates a basic magnetic field parallel to its longitudinal axis. The basic magnetic field can exhibit inhomogeneities, thus local deviations from a desired value. An examination subject— here an examined person 101—can be moved on a bed table 102 into the magnet 110. Furthermore, the MR system 100 has a gradient system 140 to generate gradient fields that are used for MR imaging and for spatial coding of acquired raw data. The gradient system 140 typically has at least three gradient coils 141 that can be controlled separately and are positioned in a well-defined manner relative to one another. The gradient coils 141 enable gradient fields to be applied and switched along defined spatial directions (gradient axes). For this purpose, gradient pulses are supplied to the gradient coils 141. For example, the pulse-like gradient fields can be used for slice selection, for frequency coding (in the readout direction) and for phase coding. A spatial coding of the raw data is thereby achieved. The spatial directions that are respectively situated parallel to the slice selection gradient fields, phase coding gradient fields and readout gradient fields do not necessarily need to be coincident with the machine coordinate system. For example, they can rather be defined relative to a k-space trajectory which can in turn be established on the basis of defined requirements of the respective MR measurement sequence and/or can be established based on anatomical properties of the examined person 101.

To excite the nuclear spins so as to deviate from alignment with the basic magnetic field (longitudinal magnetization), an RF coil arrangement 121 is provided that radiates a frequency-modulated, phase-modulated and/or amplitude-modulated RF excitation pulse (excitation pulse) into the examined person 110. A transverse magnetization of the nuclear spins is thereby generated. To generate such excitation pulses, an RF transmission unit 131 is connected via an RF mode switch 130 with the RF coil arrangement 121. The RF coil transmission unit 131 can include an RF generator and an RF modulation unit. The excitation pulses can flip the transverse magnetization out of the steady state in 1D (slice-selectively) or 2D/3D (spatially selectively or globally).

Furthermore, an RF reception unit 132 is coupled via the RF switch 130 with the RF coil arrangement 121. Via the RF reception unit 132, signals of the precessing transverse magnetization (for example via inductive injection into the RF coil arrangement 121) can be acquired as MR data.

In general, it is possible to use separate RF coil arrangements 121 for the radiation of the RF excitation pulses by means of the RF transmission unit 131 and for the acquisition of the MR data by means of the RF reception unit 132. For example, a volume coil 121 can be used for the radiation of RF pulses, and a surface coil (not drawn) which comprises an array of RF coils can be used for the acquisition of raw data. For example, the surface coil for the acquisition of the raw data can comprise 32 individual RF coils, and therefore be particularly suitable for partially parallel imaging (PPA imaging). Suitable techniques are known to those skilled in the art, such that no additional details need not to be explained here.

Furthermore, the MR system 100 has an operating unit 150 which (for example) can comprise a monitor, a keyboard, a mouse etc. Through the operating unit 150, a user entry can be received as an input and outputs can be presented to the user. For example, via the operating unit 150, individual operating modes or operating parameters of the MR system can be set by the user and/or automatically and/or via remote control.

Furthermore, the MR system 100 has a computer 160. For example, the computer 160 can be designed to accept diverse control operations within the scope of the implementation of an MR measurement sequence, for example a combined STIR-SSGR technique. The computer 160 can also be designed to evaluate acquired MR data.

The MR data can include a signal of a first spin species from a slice 80 of the examination subject 101. For example, the slice can be arranged orthogonal to a longitudinal axis of the MR system 100, thus orthogonal to a longitudinal axis of the tube 111. This direction can be coincident with the slice selection direction of the slice selection gradient fields.

Figure 2:
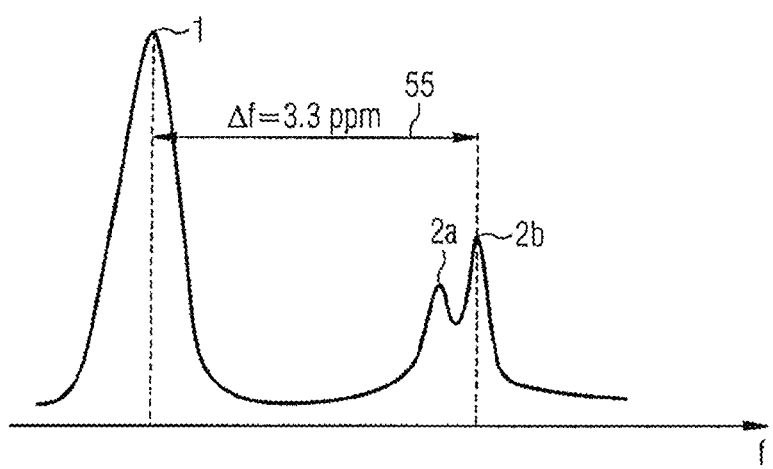
FIG. 2 shows a frequency spectrum that includes a first and second spin species that have a frequency shift.

Shown in FIG. 2 is the frequency shift 55 between the water portion (component) 1 and the fat portion 2a, 2b. The frequency shift 55 amounts to approximately 3.3 ppm. The frequency shift 55 is determined in relation to the absolute maximum of the fat portion 2a, 2b. However, the fat portion 2a, 2b has two local maxima, known as the multispectral nature of fat. These belong to a first fat portion 2a and a second fat portion 2b.

In the following, the first fat portion 2a and the second fat portion 2b are not always discussed separately. However, it should be understood that the following techniques can be applied in relation to the two fat portions 2a, 2b such that both fat portions 2a, 2b are suppressed.

Figure 3:
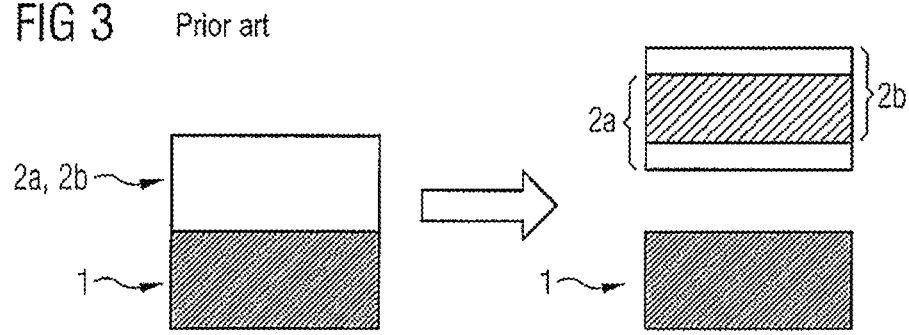
FIG. 3 illustrates the shift of image points of MR data due to the frequency shift.

From FIG. 3 it can be seen that the frequency shift 55 leads to a displacement (shift) of image points in spatial domain. This is the case because a slice selection gradient pulse is typically used for spatial coding, which slice selection gradient pulse generates a spatially variable slice selection gradient field along the slice selection direction. The nuclear spins satisfy the resonance condition only for a defined slice 80. Due to the frequency shift 55, this slice 80 is at different locations for different spin species 1, 2a, 2b. This is depicted in FIG. 3 on the right side as a displacement or incorrect mapping of the image points of the MR data.

In particular, edge artifacts can occur at edges of structures in an MR image (for example in STIR sequences without SSGR components) due to such different displacement of the different components of the fat portions 2a, 2b. The displacements can thereby occur not only along the slice selection direction but also (for example) along the phase coding direction and/or along the frequency coding direction. The cited edge artifacts can in particular occur in combination with imaging techniques that have a small pixel bandwidth along one of these directions.

Figure 4:
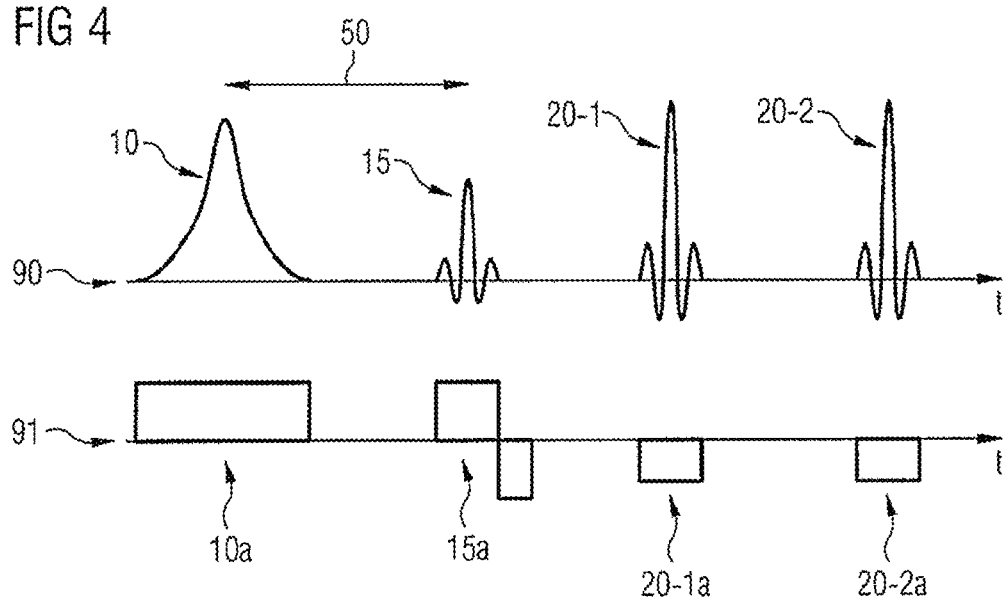
FIG. 4 shows a combined STIR-SSGR technique, wherein an inversion pulse, an excitation pulse and two refocusing pulses with associated gradient pulses are applied.

An MR measurement sequence according to a combined STIR-SSGR technique is shown in FIG. 4. The radio-frequency 90 is illustrated in FIG. 4 and the slice selection 91 is illustrated in FIG. 4 [sic]. Phase coding and readout coding are not shown.

First, a slice-selective inversion pulse 10 is radiated (for example, adiabatic pulse), accompanied by a slice selection gradient pulse 10a. In different reference implementations, the slice thickness of the spatial region inverted by means of the inversion pulse 10 is chosen to be somewhat larger than that of the slice 80 from which the MR data are acquired, namely by 20%-50%, for example. A smaller amplitude of the slice selection gradient pulse 10*a* is typically produced by a larger excited slice thickness, which in turn can increase the sensitivity to inhomogeneities of the basic magnetic field.

In various reference implementations, the amplitude of the slice selection gradient pulse 10*a* of the inversion pulse 10 also approximately corresponds to an amplitude of a slice selection gradient 15*a* of a subsequent excitation pulse 15—otherwise inversion slice and excitation slice shift given off-resonance conditions. The bandwidth of the inversion pulse 10 is also typically limited due to limitations of an amplitude of the inversion pulse 10.

The excitation pulse 15 is subsequently radiated. The slice thickness of the excited spatial region is typically somewhat greater (for example by 20%-50%) in spin echo and stimulated echo applications than the desired slice thickness of the slice 80 from which MR data are acquired. The combination of excitation pulse and refocusing pulse 20-1, 20-2 now leads to the situation that essentially nuclear spins in the slice 80 contribute to the signal. In order to keep the excitation pulse 15 as short as possible—for example to reduce echo times, and therefore to increase SNR—the bandwidth-time product can in turn not be chosen to be arbitrary large.

A first refocusing pulse 20-1 and a second refocusing pulse 20-2 are subsequently radiated. For the cited reasons, in spin echo and stimulated echo experiments the refocusing slice thickness is typically somewhat larger than the desired slice thickness of slice 80 from which MR data are acquired. The same limitations as have been explained in the preceding apply with regard to the bandwidth-time product.

In the present example, two refocusing pulses 20-1, 20-2 are shown. However, in general it would be possible to apply a different number of refocusing pulses 201-, 20-2, for example only a single refocusing pulse or even more than two refocusing pulses. In particular, in connection with diffusion coding it can be worthwhile to use two or more refocusing pulses 20-1, 20-2. However, if only a suppression of the fat portion (i.e. without diffusion coding) is sought, for example, it can be sufficient to use a single refocusing pulse 20-1.

Depending on the MR measurement sequence that is used, other pulses than the refocusing pulses 20-1, 20-2 can also be used. For example, within the scope of the diffusion coding by means of what is known as stimulated echo acquisition (stimulated echo acquisition mode, STEAM), storage pulses or restoration pulses could be used instead of the refocusing pulses 20-1, 20-2.

Figure 5:
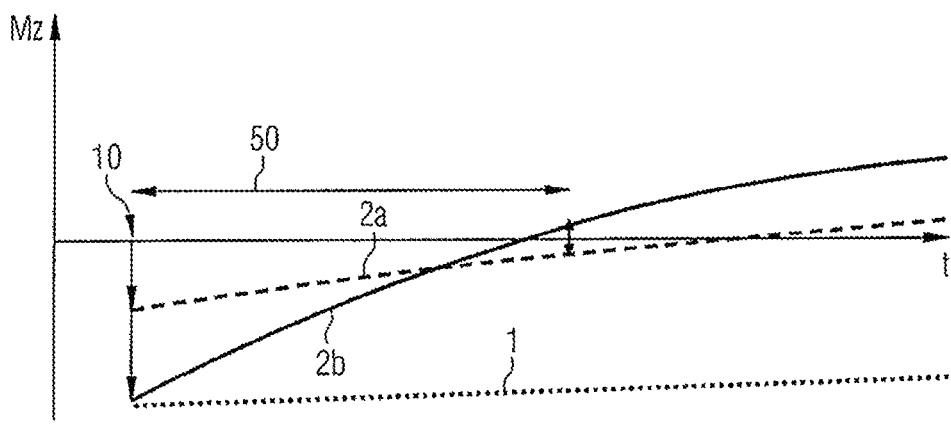
FIG. 5 illustrates a relaxation along the longitudinal direction for the inverted spin species after the inversion pulse of FIG. 2.

In the MR measurement sequence of FIG. 4, the radiation of the excitation pulse 15 takes place after a defined time period 50. The time period 50 coincides with or, respectively, correlates with the spin-lattice relaxation time of the fat portion. The time period 50 is illustrated in detail in FIG. 5. The longitudinal component of the water portion 1 (shown with the dotted line in FIG. 5) is rendered in FIG. 5 as a function of time t. As is clear from FIG. 5, the water portion 1 has the lowest T1 relaxation rate, i.e. the longest T1 relaxation time. The two fat portions 2*a*, 2*b* have different T1 relaxation rates.

The time period 50 is selected so that an optimally small portion of the second spin species is effectively excited by the excitation pulse 15. For example, the time period 50 can be selected so that the relaxing longitudinal magnetization of the second spin species has a zero crossing at the point in time of the excitation pulse 15. Insofar as both fat portions 2*a*, 2*b* are located in an image point, in spite of this an effective (total) fat signal amplitude of zero is achieved if the following condition is satisfied: $F^a(1-2\exp(-t/T_1^a))+F^b(1-2\exp(-t/T_1^b))=0$, wherein $F^a$ designates the first fat portion 2*a* and $F^b$ designates the second fat portion 2*b*, and $T_1^a$ designates the spin-lattice relaxation time of the fat portion 2*a* and $T_1^b$ designates the spin-lattice relaxation time of the fat portion 2*b*.

This effectively corresponds to the situation that, on the one hand, the more quickly relaxing portion of the second spin species has already traversed the zero crossing of the disappearing longitudinal magnetization, while on the other hand this is not yet the case for the more slowly relaxing portion of the second spin species, and the absolute magnitude of the amplitudes of the two portions of the second spin species 2*a*, 2*b* is also identical. The effective signal amplitude after the excitation therefore vectorially adds up to zero.

Figure 6:
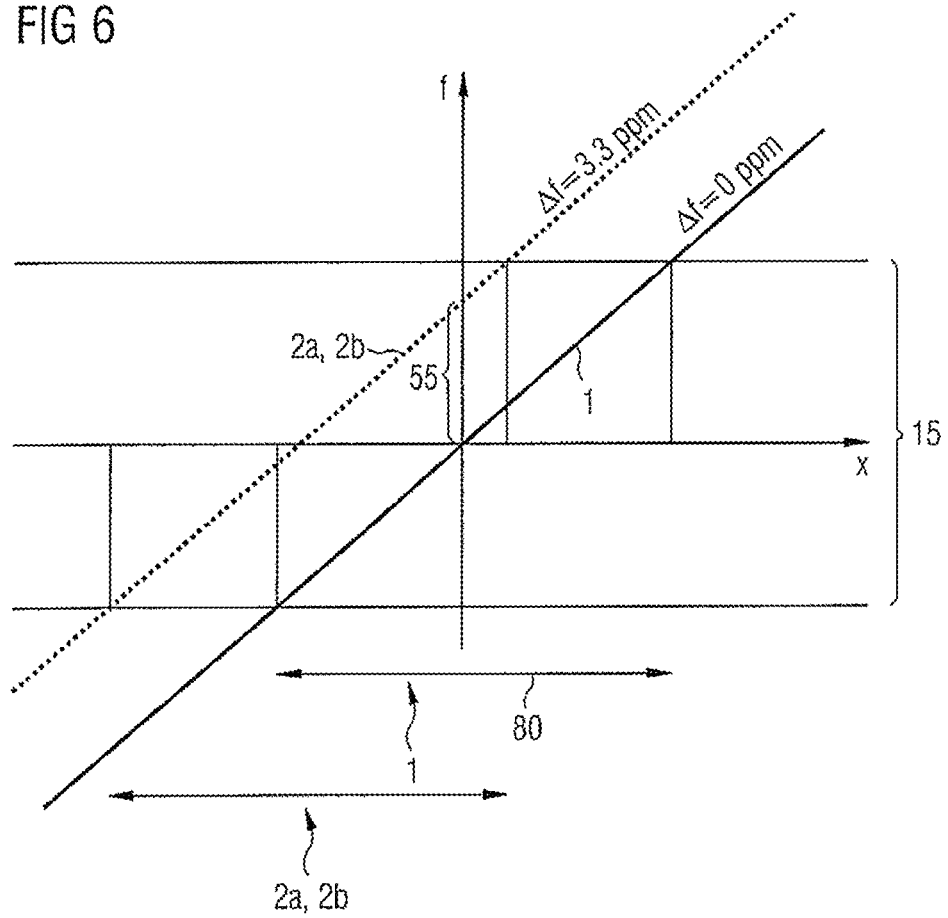
FIG. 6 illustrates the frequency shift and a slice thickness of an excited slice in a frequency/space plot.

FIG. 6 shows the slice selection for the resonant water portion 1 (solid line) and for the off-resonant fat portion 2*a*, 2*b* (dotted line). A frequency shift 44 of +3.3 ppm is drawn in FIG. 6; however, it would also be possible that a shift of −3.3 ppm is present, or, respectively, an arbitrarily different value of the frequency shift 55. In FIG. 6, the local resonance frequency f is represented as a function of the location x. The local resonance frequency f is affected by a slice selection gradient field. A larger (smaller) sample of the associated slice selection gradient pulse generates a larger (smaller) gradient field, whereby the slope of the straight lines in FIG. 6 is greater (smaller). For example, the excitation pulse 15 excites in the marked frequency range (bandwidth) so that the transverse magnetization for the water portion 1 and the fat portion 2*a* and 2*b* are excited (indicated below in FIG. 6 with horizontal arrows) in different spatial domain regions. For the case that the excitation pulse 15 has a slice thickness that is equal to that of the slice 80 for which the MR data are acquired, this spatial domain region corresponds to the slice 80 (as indicated in FIG. 6).

The width of the spatial region excited by an RF pulse can be controlled by a change of the gradient field or, respectively, the amplitude of the gradient pulse, as well as via the bandwidth. A larger bandwidth produces a larger width of the excited spatial region. A larger bandwidth typically produces a shorter pulse duration, which can in turn increase an amplitude of the RF pulse given the same flip angles, which in turn results in an increased SAR (see bandwidth-time product). A smaller gradient field produces a larger width of the excited spatial region. A smaller gradient field typically produces a higher sensitivity to inhomogeneities of the basic magnetic field, whereby artifacts are promoted.

These problems produce limitations in the suppression of the residual fat signal. Techniques are shown in the following which—in spite of these problems—enable the residual signal of the fat portion 2*a*, 2*b* to be further suppressed. One cause of the residual fat signal is initially discussed with regard to FIG. 7.

Figure 7:
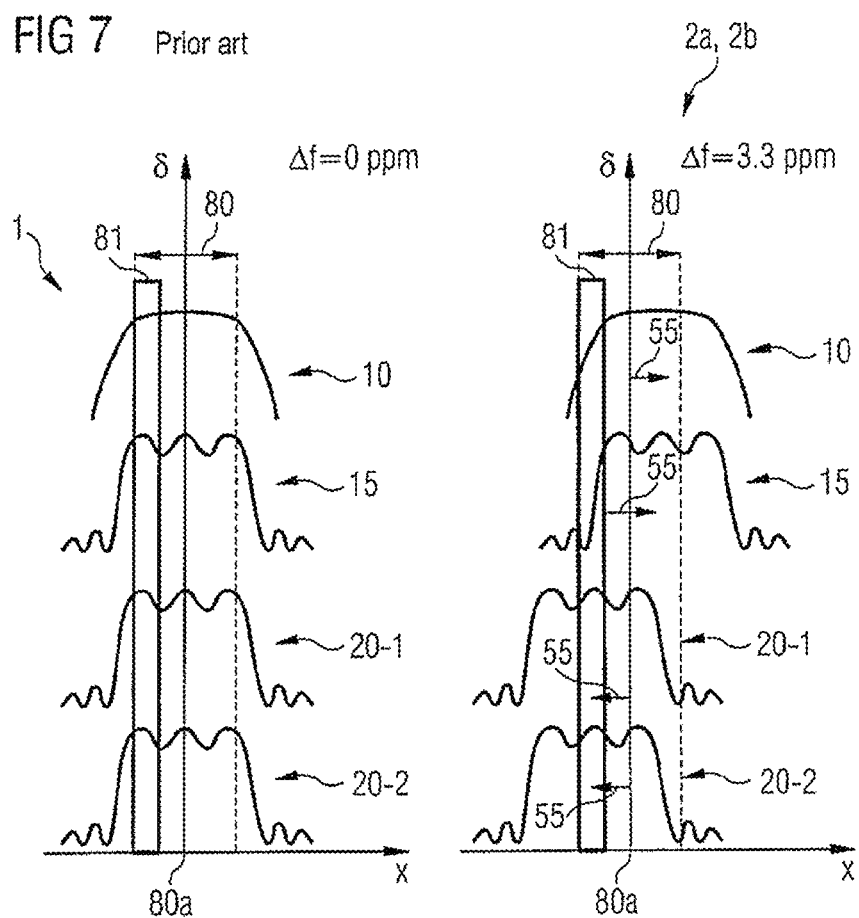
FIG. 7 shows spatial domain profiles of a flip angle for the RF pulses of FIG. 4 along the slice selection direction for two spin species.

Rendered on the left in FIG. 7 is the flip angle δ of nuclear spins of the water portion 1 for the inversion pulse 10, the excitation pulse 15 and the two refocusing pulses 20-1, 20-2, depending on the position X along the slice normal (see FIG. 4). This dependency inasmuch represents the spatial or frequency profile of the corresponding RF pulse 10, 15, 20-1, 20-2. The spatial and frequency domains here are to be considered to be identical since a distinct precession frequency of the nuclear spins can be associated with each location via an applied slice selection gradient field. The spatial or frequency domain profile of the RF pulse 10, 15, 20-1, 20-2 is typically linked with the time period pulse shape of the corresponding RF pulse 10, 15, 20-1, 20-2 according to the Fourier transformation rule. For example, the flip angle δ in FIG. 7 can respectively be shown normalized to a maximum. For example, a precise determination of the flip angle δ and its spatial dependency can be calculated using what are known as Bloch simulations for a given time period pulse shape, for example in a preceding analysis step.

Rendered on the right in FIG. 7 is the flip angle δ of nuclear spins of the fat portion 2a, 3b for the inversion pulse 10, the excitation pulse 15 and the two refocusing pulses 20-1, 20-2 according to the MR measurement sequence of FIG. 4. On the scale of FIG. 7, no difference results for the first and second fat portion 2a, 2b. The slice 80 for which MR data of the first spin species are acquired is also illustrated in FIG. 7. For the regions in which the RF pulses 10, 15, 20-1, 20-2 have edges outside of the slice 80, no significant signal contribution of the water portion 1 results given a combined consideration of the corresponding flip angles δ. A partial region 81 of the slice 80 is also drawn in FIG. 7. The partial region 80 extends on one side of the middle 80a up to the edge of the slice 80.

As can be seen from FIG. 7, the pulses 10, 15, 20-1, 20-2 for the water portion 1 are symmetrical relative to a middle 80a of the slice 80. This applies not only to the fat portion 2a, 2b. Due to the frequency shift 44 (indicated with horizontal arrows in FIG. 7), for the fat portion 2a, 2b the spatial domain profiles of the pulses 10, 15, 20-1, 20-2 are shifted relative to the middle 80a of the slice 80, and in fact to the right (left) for negative (positive) amplitudes of the slice selection gradient pulses 10a, 15a, 20-1a, 20-2a (see FIG. 4). In general, relative to the refocusing pulses 20-1, 20-2, a corresponding relative shift of the spatial domain profiles of the excitation pulse 15 relative to one another also occurs if the amplitudes of the associated gradient pulses 15a, 20-1a, 20-2a are chosen to be sufficiently different, wherein different polarities are not necessary. The spatial domain profiles of the excitation pulse 15 and the refocusing pulses 20-1, 20-2 partially overlap, which is why a partial SSGR technique is used.

Figure 8:
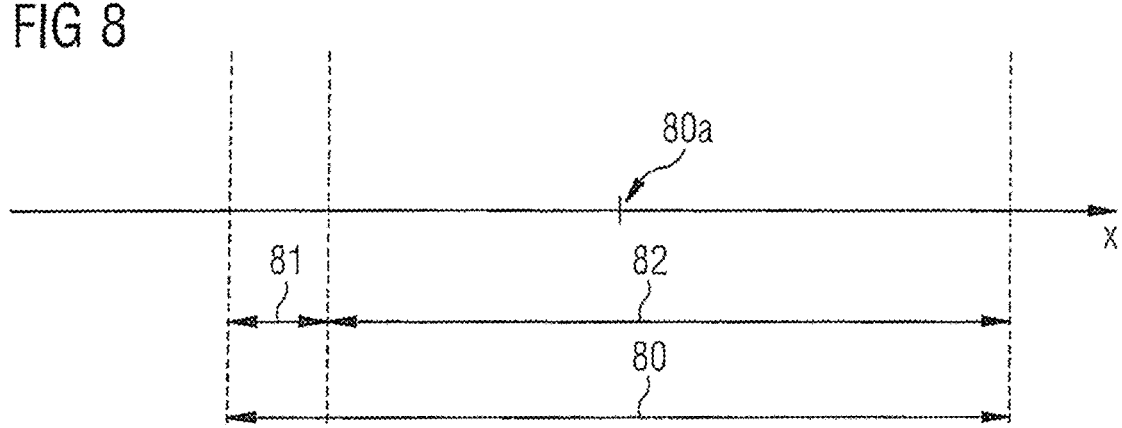
FIG. 8 illustrates a slice for which MR data are acquired and that includes a central region and a partial region.

The geometric arrangement of the partial region 81 of the slice 80 is depicted enlarged in FIG. 8. From FIG. 8 it is clear that the partial region 81 adjoins a central region 82 that includes the middle 80a of the slice. The central region 82 extends on one side of the slice up to its edge. On the other side of the slice 80, the partial region 71 extends up to the edge of the slice 80. In the central region 82, the inversion pulse 10, the excitation pulse 15 and the two refocusing pulses 20-1, 20-2 have approximately the same flip angles. Depending on the strength of the frequency shift 55, it can occur that there is no central region 82. However, the partial region 81 generally does not need to extend up to the edge of the slice 80.

Referring again to FIG. 7, from a comparison of the right side with the left side it is clear that—in the partial region 81 of the slice 80—the inversion pulse 10 for the water portion 1 and the fat portion 2a, 2b has different flip angles δ due to the frequency shift 55. Namely, in the partial region 81 of the slice 80 the flip angle δ of the inversion pulse 10 for the fat portion 2a, 2b already significantly decreases from its maximum value, meaning that the edge of the inversion pulse 10 is located there.

Therefore, the entire magnetization of the fat portion 2a, 2b is not inverted, and the residual magnetization of the fat portion 2a, 2b remains at the steady state at the point in time of the excitation due to the incomplete inversion. Because the excitation pulse 15 has a finite flip angle δ in the partial region 81, at least one portion of the residual magnetization of the fat portion 2a, 2b is deflected by the excitation pulse 15 and is subsequently manipulated by the refocusing pulses 20-1, 20-2 to form an echo. Therefore, a residual fat signal is present in the MR data in the reference implementation shown in FIG. 7.

Figure 9:
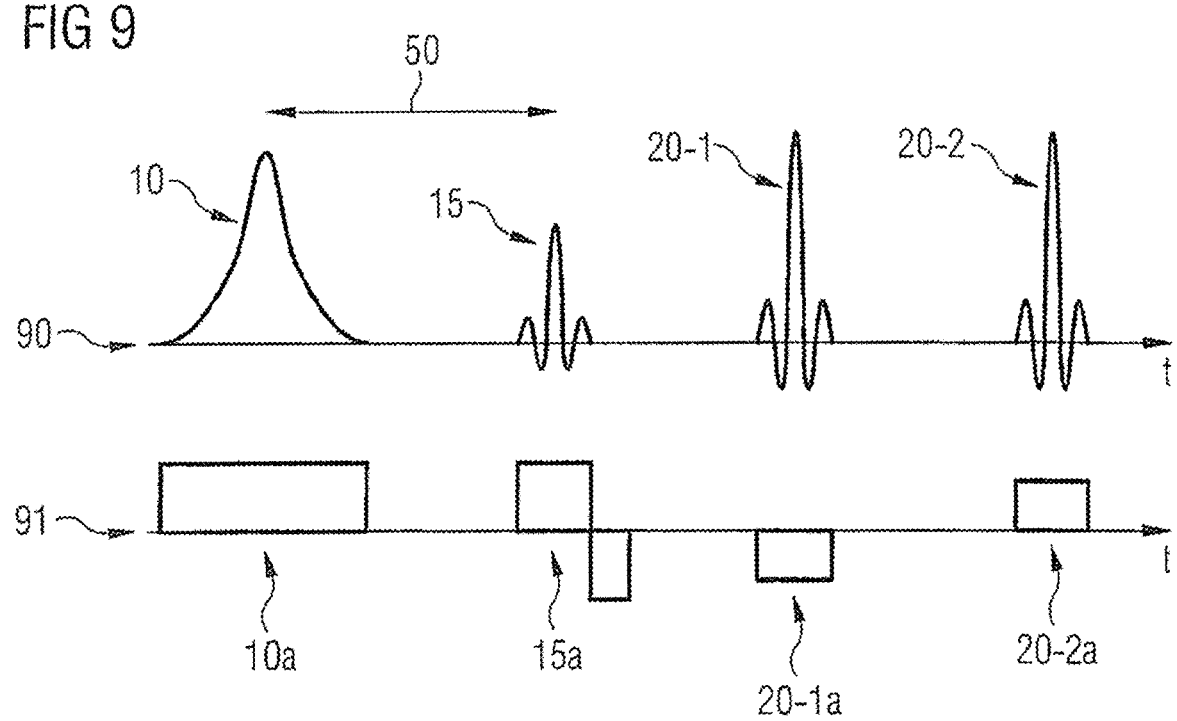
FIG. 9 shows a combined STIR-SSGR technique according to different embodiments.

An MR measurement sequence according to different embodiments is depicted in FIG. 9. The amplitude of the gradient pulse 20-1a of the first refocusing pulse 20-1 has a different polarity but the same magnitude as the amplitude of the gradient pulse 20-2a of the refocusing pulse 20-2. In general, it would be possible that the amplitudes of the gradient pulses 20-1a, 20-2a assume different values, wherein the polarities can be the same or different. From the comparison of FIGS. 4 and 9 it is also clear that the gradient pulse 20-2a of the second refocusing pulse 20-2 has an inverted polarity.

In FIG. 10, the spatial domain profile of the flip angle δ for the MR measurement sequence of FIG. 9 is shown for the fat portion 2a, 2b. FIG. 4, continuing to the left, applies to the water portion 1. The first refocusing pulse 20-1 (second refocusing pulse 20-2) has no (an) edge in the partial region 81. The edge of the second refocusing pulse 20-2 is marked with a thick vertical arrow. An additional suppression of the fat portion 2a, 2b takes place there due to the reduced flip angle.

Generally formulated, in the partial region 81 at least one of the at least two refocusing pulses 20-1, 20-2 can have a smaller flip angle for the fat portion 2a, 2b than for the water portion 1. As can be seen from a comparison of the left of FIG. 4 with FIG. 10, both refocusing pulses 20-1, 20-2 have a relatively large flip angle δ in the partial region 81 for the water portion 1 while the flip angle of the second refocusing pulse 20-2 already declines for the fat portion 2a, 2b in the partial region 81. This is the case because the frequency shift 55 for the refocusing pulses 20-1, 20-2 is oriented in the opposite direction. In particular, the excitation pulse 15 and the second refocusing pulse have an identically oriented frequency shift 55.

An additional scenario of the suppression of the residual fat signal from the partial region 81 is illustrated in FIG. 11. In this scenario, the inversion pulse 10 for the water portion 1 and the fat portion 2a, 2b have comparable flip angles δ in the entire slice 80. The plateau of the inversion pulse 10 is widened (see FIGS. 4 and 11). The spatial domain profile of the flip angle δ of the inversion pulse 10 for the water portion 1 is also asymmetrical relative to the middle 80a of the slice 80. The spatial domain profile of the flip angle δ of the inversion pulse 10 has a greater extent counter to the direction of the frequency shift 55 of the second spin species 2a relative to the first spin species 1 for the inversion pulse 10.

Through the one-sided widening of the inversion pulse 10, on the one hand an improved suppression of the residual fat signal from the partial region 81 can be achieved because now nearly the entire magnetization is inverted there, and then is suppressed within the scope of the STIR component of the MR measurement sequence. Moreover, it is simultaneously achieved that the requirements for the inversion pulse 19 are tightened only slightly with regard to amplitude of the gradient pulse 10a, amplitude of the inversion pulse 10, bandwidth etc. In particular, a (typically unnecessary) widening of the spatial domain profile of the inversion pulse 10 along the direction of the frequency shift 55 is foregone.

An additional scenario for suppression of the residual fat signal from the partial region 81 is illustrated in FIGS. 12 and 13: in the partial region 81 of the slice 80, the excitation pulse 15 has a disappearing flip angle δ. This is achieved in FIG. 12 by a particularly sharp edge of the excitation pulse 15 (marked with the vertical arrow), wherein the plateau of the excitation pulse 15 remains unchanged relative to the reference implementation of FIGS. 4 and 7, for example. In contrast to this, the plateau of the excitation pulse 15 is reduced in FIG. 13, for example given consistent edge steepness.

A sharper edge can typically require a longer RF pulse. This can extend an echo time at which an echo can be formed, whereby a signal-to-noise ratio can in turn be reduced. Therefore, it can in principle be worthwhile to only design the left edge of the excitation pulse 15—i.e. that edge that is opposite the direction of the frequency shift 55 of the excitation pulse 15 for the fat portion 2a, 2b relative to the water portion 1—to be particularly steep. In particular, it can be possible that the spatial domain profile of the flip angle δ of the excitation pulse 15 has an edge width that is smaller than the edge width of a spatial domain profile of the flip angle δ of the refocusing pulses 20-1, 20-2.

For example, it is possible that the excitation pulse 15 excites the transverse magnetization in a slice thickness that is smaller than the slice thickness in which the at least one manipulation pulse 20-1, 20-2 refocuses the transverse magnetization with finite flip angle δ (see FIG. 13). For example, the excitation pulse 15 can excite the transverse magnetization in a slice thickness with finite flip angle δ, which is approximately equal to the width of the slice 80. This allows the signal of the water portion 1 to be obtained uniformly over the entire width of the slice 80, although the excitation pulse 15 excites a comparably small slice thickness.

In FIG. 13, the refocusing pulses also have a widened slice thickness which ensures that uniform signal of the water portion is achieved along the entire slice 80.

The edge of the excitation pulse 15 of FIG. 13 corresponds approximately to that of the excitation pulse of FIG. 7.

A flowchart of an embodiment of the method according to different aspects of the present invention is shown in FIG. 14. The method begins with Step S1. In Step S2, the inversion pulse 10 is initially radiated. For example, the inversion pulse 10 can be widened asymmetrically, such that in the entire slice 80 both the water portion 1 and the fat portion 2a, 2b is [sic] inverted uniformly and completely.

The radiation of the excitation pulse 15 takes place in Step S3. For example, the excitation pulse can have no or only a small flip angle δ in the partial region 81 for the fat portion 2a, 2b. For example, this can be achieved by a relatively small slice thickness and/or by a particularly steep edge of the excitation pulse 15.

The radiation of the at least one manipulation pulse 20-1, 20-2 takes place in Step S4. For example, the accompanying slice selection gradient pulses 20-1a, 20-2a can have amplitudes with different values and/or different polarities. This causes for the fat portion 2a, 2b, at least one of the refocusing pulses 20-1, 20-2 to have a reduced flip angle δ in the partial region 81 for the fat portion 2a, 2b.

In Step S5, the MR data are acquired, respectively at the echoes that are formed by the refocusing pulses 20-1, 20-2 of the Step S4.

The method ends in Step S6. Another water MR image could optionally be provided, for example on the monitor 150.

For example, in the workflow of step S2 described in the preceding an additional, optional step could be implemented that includes: analysis of the spatial domain profile of the flip angle δ of the inversion pulse 10 and/or of the excitation pulse 15 and/or of the at least one refocusing pulse 20-1, 20-2. Depending on the analysis, one or more measures that have been described in the preceding with regard to S2, S3, S4 can then be implemented. For example, in step S4 the inversion pulse could be widened if it is established in the analysis step that the spatial domain profile of the inversion pulse 10 promotes a significant residual magnetization in the partial region. Alternatively or additionally, for example, in step S3 the flip angle of the excitation pulse 15 could selectively be reduced in the partial region 81 depending on a corresponding result of the analysis step. Alternatively or additionally, for example, in step S4 at least one of the refocusing pulses 20-1, 20-2 could be adapted so that these have a reduced flip angle in the partial region 81, depending on the result of the analysis step.

In FIG. 15-17, additional scenarios are illustrated for a comprehensive suppression of the fat portion 2a, 2b. A scenario comparable to FIG. 10 is shown in FIG. 15. In FIG. 15, the frequency shift 55 is greater than as in FIG. 10; the various RF pulses 10, 15, 20-1, 20-2 therefore exhibit a greater offset relative to the middle point 80a of the slice 80 for which MR data of the water portion 1 are acquired.

In the scenario of FIG. 15, the second refocusing pulse 20-2 is also inverted, meaning that it has an amplitude with the opposite polarity as (for example) the excitation pulse 15 and in particular the first refocusing pulse 20-1, while in FIG. 10 the first refocusing pulse 20-1 is inverted. The second refocusing pulse 20-2 also exhibits a smaller (in terms of absolute value) frequency shift 55 than the first refocusing pulse 20-1, for example.

In such a scenario, an improved suppression of the fat signal in the MR data can again take place. In this scenario, the partial region 81 extends into the center of the slice 80 (does not adjoin the edge of the slice 80, in contrast to FIG. 10).

If the second refocusing pulse 20-2 were still to have a somewhat larger frequency shift 55—for example due to selection of a correspondingly reduced amplitude of the slice selection gradient pulse 20-2a—a partial SSGR component would no longer exist; rather, a complete SSGR component would be present, i.e., in such a case the spatial domain profiles of the flip angle δ of the two refocusing pulses 20-1, 20-2 would no longer overlap.

In FIG. 16, a scenario comparable to FIG. 11 is illustrated in which the inversion pulse 10 is widened asymmetrically, for example relative to the excitation pulse 15 (marked with the vertical arrow in FIG. 16). In FIG. 16, the partial region 80 does not lie at an edge of the slice 80.

In FIG. 17, an additional scenario is illustrated in which the amplitudes of the gradient pulses 10a, 15a, 20-1a, 20-2a all have the same polarity. Therefore, the frequency shift 55 (to the right in FIG. 16) for the spatial domain profiles of the flip angle δ is oriented in the same direction (to the right in FIG. 16) for all RF pulses 10, 15, 20-1, 20-2. A partial overlap of the spatial domain profiles of the flip angle δ of the various RF pulses 10, 15, 20-1, 20-2 (thus a partial SSGR component) is also present in FIG. 16.

An edge region 85 is shown in FIG. 17. The edge region 85 corresponds to the partial region 81, wherein the edge region 85 is arranged outside of the slice 80. In the edge region 85, the inversion pulse 10 for the water portion 1 and that for the fat portion 2a, 2b have different flip angles δ. The spatial domain profile of the flip angle δ of the inversion pulse 10 also has an edge in the edge region 85 for the fat portion 2a, 2b. In FIG. 17, the spatial domain profile of the flip angle δ of the excitation pulse 15 also has finite flip angles δ (i.e. flip angles δ significantly greater than zero) for the fat portion 2a, 2b.

The suppression of the fat signal is achieved in FIG. 17 in that one of the two refocusing pulses 20-1, 20-2 in the edge region 85 has a spatial domain profile of the flip angle δ with an edge. This is achieved because the amplitudes of the slice selection gradient pulses 20-1a, 20-2a of the two refocusing pulses 20-1, 20-2 are different. Only the first refocusing pulse 20-1 is frequency-shifted relative to the excitation pulse 15 for the fat portion 2a, 2b. A more complete suppression of the fat signal is achieved by the doubled edge in the partial region 85, namely of the excitation pulse 15 and of the second refocusing pulse 20-2.

The edge region 85 is characterized in that a complete inversion of the fat portion 2a, 2b does not take place in the edge region 85, for example because there the inversion pulse 85 has a flip angle<180°, thus an edge or disappearing angle δ. If the excitation pulse 15 in the edge region 85 simultaneously has a significant, finite flip angle δ in the edge region 85, an excitation of the residual magnetization of the fat portion 2a, 2b takes place. Corresponding concepts also apply—as presented in the preceding—to the partial region 81 that lies within the slice, which is why the concepts that were explained in the preceding with regard to the partial region 81 may also be directly transferred to the edge region 85. In general, corresponding definitions of the partial region 81—for example different flip angles of the inversion pulse 10 for the fat portion 2a, 2b and the water portion 1—can also be transferred to the edge region 85 insofar as this lies within the slice 80.

In general, a variety of techniques that have been explained in the preceding with regard to the partial region 81 within the slice 80 can be transferred directly to the edge region 85 (which can be situated inside and/or outside of the slice 80). For example, it would thus be possible that the excitation pulse 15 has disappearing flip angles δ in the edge region 85 in which the inversion pulse 10 has an edge, for example in that it excites a smaller (in comparison to the inversion pulse 10) spatial domain region along the slice selection direction and/or in that the excitation pulse 15 has particularly sharp edges. It would also be possible that the inversion pulse 10 is widened such that there is no longer a region in which the excitation pulse 15 has finite, significant flip angles δ and the inversion pulse 10 has flip angles δ<180°. In other words: a spatial domain profile of the flip angle δ of the inversion pulse 10 for the fat portion 2a, 2b can have a maximized flip angle δ (thus produce an essentially complete inversion with residual magnetization) in a region in which the excitation pulse 15 for the fat portion 2a, 2b has finite flip angles δ. In particular, the spatial domain profile of the flip angle δ of the inversion pulse 10 for the water potion 1 can be asymmetrical relative to the middle 80a of the slice 80 (see FIGS. 11 and 16).

In the preceding, techniques have been described that enable a suppression of the residual fat signal given combined STIR-SSGR techniques. In general, such techniques can be flexibly applied to the most varied measurement protocols. Naturally, the features of the embodiments and aspects of the invention that are described in the preceding can be combined with one another. In particular, the features can be used not only in the described combinations but also in other combinations or independently, without departing from the scope of the invention.

For example, it would also be possible to use what are known as slice multiplexing techniques in order to acquire at least partially parallel MR data from multiple slices. The corresponding techniques can be used directly for individual slices of the appertaining slices.

Although further modifications and changes may be suggested by those skilled in the art, it is the intention of the inventor to embody within the patent warranted hereon all changes and modifications as reasonably and properly come within the scope of his contribution to the art.

I claim as my invention:

1. A method to acquire magnetic resonance data from nuclear spins in a slice of an examination subject, said slice comprising nuclear spins of a first spin species and a second spin species exhibiting a frequency shift relative to each other and having respectively different spin-lattice relaxation times, said method comprising:
    operating a magnetic resonance apparatus with the examination subject situated therein, to apply an inversion pulse that acts on a longitudinal magnetization of said first spin species in said slice and on a longitudinal magnetization of said second spin species in said slice;
    after a predetermined time period that is dependent on said spin-lattice relaxation time of said second spin species, operating said magnetic resonance apparatus to apply an excitation pulse and an associated first gradient pulse, that produce a transverse magnetization of said nuclear spins in said slice;
    after applying said excitation pulse and said associated first gradient pulse, operating said magnetic resonance apparatus to apply at least one manipulation pulse and an associated second gradient pulse, that produce at least one echo of said transverse magnetization of at least said first spin species, said second gradient pulse having an amplitude that is different from an amplitude of said first gradient pulse;
    operating said magnetic resonance apparatus to acquire magnetic resonance data from an entirety of said slice during said at least one echo;
    operating said magnetic resonance apparatus to suppress signals from said second spin species in the acquired magnetic resonance data by, in a partial region of said slice, applying said inversion pulse with different flip angles for said first spin species and said second spin species due to said frequency shift, and applying said excitation pulse with a disappearing flip angle for said second spin species; and
    processing the acquired magnetic resonance data in a computerized processor to generate an electronic signal having a format from which a magnetic resonance image of said slice can be generated, said magnetic resonance image comprising substantially only signal contributions that originate from said first spin species, and making said electronic signal available at an output of said processor.

2. A method as claimed in claim 1, comprising:
    operating said magnetic resonance apparatus to apply said excitation pulse with a spatial domain profile of the flip angle thereof having an edge width that is smaller than an edge width of a spatial domain profile of the flip angle of said at least one manipulation pulse.

3. A method as claimed in claim 1, comprising:
    operating said magnetic resonance apparatus to apply said excitation pulse to excite transverse magnetization in a slice thickness of said slice with a finite flip angle, said slice thickness being smaller than a slice thickness in which said at least one manipulation pulse refocuses the transverse magnetization with a finite flip angle.

4. A method as claimed in claim 1, comprising:
operating said magnetic resonance apparatus to apply said excitation pulse to excite transverse magnetization in a slice thickness of said slice with a finite flip angle, said slice thickness being approximately equal to a total width of said slice.

5. A method as claimed in claim 1, comprising operating said magnetic resonance apparatus to apply said at least one manipulation pulse to refocus the transverse magnetization in a slice thickness of said examination subject with a finite flip angle, said slice thickness being larger by a factor of 1.5 or by a factor of 2 than a total width of said slice.

6. A method to acquire magnetic resonance data from nuclear spins in a slice of an examination subject, said slice comprising nuclear spins of a first spin species and a second spin species exhibiting a frequency shift relative to each other and having respectively different spin-lattice relaxation times, said method comprising:
operating a magnetic resonance apparatus with the examination subject situated therein, to apply an inversion pulse that acts on a longitudinal magnetization of said first spin species in said slice and on a longitudinal magnetization of said second spin species in said slice;
after a predetermined time period that is dependent on said spin-lattice relaxation time of said second spin species, operating said magnetic resonance apparatus to apply an excitation pulse and an associated first gradient pulse, that produce a transverse magnetization of said nuclear spins in said slice;
after applying said excitation pulse and said associated first gradient pulse, operating said magnetic resonance apparatus to apply at least one manipulation pulse and an associated second gradient pulse, that produce at least one echo of said transverse magnetization of at least said first spin species, said second gradient pulse having an amplitude that is different from an amplitude of said first gradient pulse;
operating said magnetic resonance apparatus to acquire magnetic resonance data from an entirety of said slice during said at least one echo;
operating said magnetic resonance apparatus to suppress signals from said second spin species in the acquired magnetic resonance data by applying said inversion pulse with a spatial domain profile of a flip angle thereof for said first spin species that is asymmetrical relative to a middle of said slice; and
processing the acquired magnetic resonance data in a computerized processor to generate an electronic signal having a format from which a magnetic resonance image of said slice can be generated, said magnetic resonance image comprising substantially only signal contributions that originate from said first spin species, and making said electronic signal available at an output of said processor.

7. A method as claimed in claim 6 comprising:
operating said magnetic resonance apparatus to apply said inversion pulse with said spatial domain profile of said flip angle having a greater extent opposite to a direction of said frequency shift of said second spin species relative to said first spin species, than along said direction of said frequency shift of said second spin species relative to said first spin species.

8. A method to acquire magnetic resonance data from nuclear spins in a slice of an examination subject, said slice comprising nuclear spins of a first spin species and a second spin species exhibiting a frequency shift relative to each other and having respectively different spin-lattice relaxation times, said method comprising:
operating a magnetic resonance apparatus with the examination subject situated therein, to apply an inversion pulse that acts on a longitudinal magnetization of said first spin species in said slice and on a longitudinal magnetization of said second spin species in said slice;
after a predetermined time period that is dependent on said spin-lattice relaxation time of said second spin species, operating said magnetic resonance apparatus to apply an excitation pulse and an associated first gradient pulse, that produce a transverse magnetization of said nuclear spins in said slice;
after applying said excitation pulse and said associated first gradient pulse, operating said magnetic resonance apparatus to apply at least two manipulation pulses each with an associated second gradient pulse, that produce at least one echo of said transverse magnetization of at least said first spin species, each second gradient pulse having an amplitude that is different from an amplitude of said first gradient pulse;
operating said magnetic resonance apparatus to acquire magnetic resonance data from an entirety of said slice during said at least one echo;
operating said magnetic resonance apparatus to suppress signals from said second spin species in the acquired magnetic resonance data by applying said inversion pulse with a spatial domain profile of a flip angle thereof for said second spin species that, in an edge region of said slice, has an edge or a disappearing flip angle, and applying said excitation pulse with finite flip angles for said second spin species, and applying at least one of said at least two manipulation pulses, and said excitation pulse, with a spatial domain profile of the respective flip angles thereof having an edge; and
processing the acquired magnetic resonance data in a computerized processor to generate an electronic signal having a format from which a magnetic resonance image of said slice can be generated, said magnetic resonance image comprising substantially only signal contributions that originate from said first spin species, and making said electronic signal available at an output of said processor.

9. A method as claimed in claim 8, comprising:
operating said magnetic resonance apparatus to apply said at least two manipulation pulses as a first manipulation pulse and a second manipulation pulse, and applying said second gradient pulse as one second gradient pulse associated with said first manipulation pulse and another second gradient pulse associated with said second manipulation pulse, and with said one second gradient pulse having an amplitude that is different from said another second gradient pulse.

10. A method as claimed in claim 9 comprising:
operating said magnetic resonance apparatus to apply said first and second manipulation pulses to refocus the transverse magnetization in respective, substantially identical slice thicknesses of said slice with a finite flip angle.

11. A method as claimed in claim 10 comprising operating said magnetic resonance apparatus to apply said excitation pulse with a disappearing flip angle in said edge region.

12. A method to acquire magnetic resonance data from nuclear spins in a slice of an examination subject, said slice comprising nuclear spins of a first spin species and a second spin species exhibiting a frequency shift relative to each other and having respectively different spin-lattice relaxation times, said method comprising:

operating a magnetic resonance apparatus with in which the examination subject situated therein, to apply an inversion pulse that acts on a longitudinal magnetization of said first spin species in said slice and on a longitudinal magnetization of said second spin species in said slice;

after a predetermined time period that is dependent on said spin-lattice relaxation time of said second spin species, operating said magnetic resonance apparatus to apply an excitation pulse and an associated first gradient pulse, that produce a transverse magnetization of said nuclear spins in said slice;

after applying said excitation pulse and said associated first gradient pulse, operating said magnetic resonance apparatus to apply at least one manipulation pulse and an associated second gradient pulse, that produce at least one echo of said transverse magnetization of at least said first spin species, said second gradient pulse having an amplitude that is different from an amplitude of said first gradient pulse;

operating said magnetic resonance apparatus to acquire magnetic resonance data from an entirety of said slice during said at least one echo;

operating said magnetic resonance apparatus to suppress signals from said second spin species in the acquired magnetic resonance data by applying said inversion pulse with a spatial domain profile of the flip angle thereof for said seconds spin species that, in an edge region of said slice, has an edge or a disappearing flip angle, and applying said excitation pulse with a disappearing flip angle for said second spin species; and processing the acquired magnetic resonance data in a computerized processor to generate an electronic signal having a format from which a magnetic resonance image of said slice can be generated, said magnetic resonance image comprising substantially only signal contributions that originate from said first spin species, and making said electronic signal available at an output of said processor.

13. A method as claimed in claim 12, comprising:
operating said magnetic resonance apparatus to apply said excitation pulse with a spatial domain profile of the flip angle thereof having an edge width that is smaller than an edge width of a spatial domain profile of the flip angle of said at least one manipulation pulse.

14. A method as claimed in claim 12, comprising:
operating said magnetic resonance apparatus to apply said excitation pulse to excite transverse magnetization in a slice thickness of said slice with a finite flip angle, said slice thickness being smaller than a slice thickness in which said at least one manipulation pulse refocuses the transverse magnetization with a finite flip angle.

15. A method as claimed in claim 12, comprising:
operating said magnetic resonance apparatus to apply said excitation pulse to excite transverse magnetization in a slice thickness of said slice with a finite flip angle, said slice thickness being approximately equal to a total width of said slice.

16. A method as claimed in claim 12, comprising
operating said magnetic resonance apparatus to apply said at least one manipulation pulse to refocus the transverse magnetization in a slice thickness of said examination subject with a finite flip angle, said slice thickness being larger by a factor of 1.5 or by a factor of 2 than a total width of said slice.

17. A method to acquire magnetic resonance data from nuclear spins in a slice of an examination subject, said slice comprising nuclear spins of a first spin species and a second spin species exhibiting a frequency shift relative to each other and having respectively different spin-lattice relaxation times, said method comprising:

operating a magnetic resonance apparatus with the examination subject situated therein, to apply an inversion pulse that acts on a longitudinal magnetization of said first spin species in said slice and on a longitudinal magnetization of said second spin species in said slice;

after a predetermined time period that is dependent on said spin-lattice relaxation time of said second spin species, operating said magnetic resonance apparatus to apply an excitation pulse and an associated first gradient pulse, that produce a transverse magnetization of said nuclear spins in said slice;

after applying said excitation pulse and said associated first gradient pulse, operating said magnetic resonance apparatus to apply at least one manipulation pulse and an associated second gradient pulse, that produce at least one echo of said transverse magnetization of at least said first spin species, said second gradient pulse having an amplitude that is different from an amplitude of said first gradient pulse;

operating said magnetic resonance apparatus to acquire magnetic resonance data from an entirety of said slice during said at least one echo;

operating said magnetic resonance apparatus to suppress signals from said second spin species in the acquired magnetic resonance data by applying said inversion pulse with a spatial domain profile of the flip angle thereof for said second spin species that has a maximized flip angle in a region in which said excitation pulse has finite flip angles for said second spin species, and applying said inversion pulse with a spatial domain profile of the flip angle thereof for said first spin species that is asymmetrical relative to a middle of said slice; and processing the acquired magnetic resonance data in a computerized processor to generate an electronic signal having a format from which a magnetic resonance image of said slice can be generated, said magnetic resonance image comprising substantially only signal contributions that originate from said first spin species, and making said electronic signal available at an output of said processor.

18. A method as claimed in claim 17 comprising:
operating said magnetic resonance apparatus to apply said inversion pulse with said spatial domain profile of said flip angle having a greater extent opposite to a direction of said frequency shift of said second spin species relative to said first spin species, than along said direction of said frequency shift of said second spin species relative to said first spin species.

19. A magnetic resonance apparatus configured to acquire magnetic resonance data from nuclear spins in a slice of an examination subject, said slice comprising nuclear spins of a first spin species and a second spin species exhibiting a frequency shift relative to each other and having respectively different spin-lattice relaxation times, said apparatus comprising:

a magnetic resonance data acquisition unit;
a control unit configured to operate a magnetic resonance data acquisition unit, in which the examination subject is situated, to apply an inversion pulse that acts on a longitudinal magnetization of said first spin species in said slice and on a longitudinal magnetization of said second spin species in said slice;

said control unit being configured after a predetermined time period that is dependent on said spin-lattice relaxation time of said second spin species, to operate said magnetic resonance data acquisition unit to apply an excitation pulse and an associated first gradient pulse, that produce a transverse magnetization of said nuclear spins in said slice;

said control unit being configured after applying said excitation pulse and said associated first gradient pulse, to operate said magnetic resonance data acquisition unit to apply at least one manipulation pulse and an associated second gradient pulse, that produce at least one echo of said transverse magnetization of at least said first spin species, said second gradient pulse having an amplitude that is different from an amplitude of said first gradient pulse;

said control unit being configured to operate said magnetic resonance data acquisition unit to acquire magnetic resonance data from an entirety of said slice during said at least one echo;

said control unit being configured to operate said magnetic resonance data acquisition unit to suppress signals from said second spin species in the acquired magnetic resonance data by, applying said inversion pulse in a partial region of said slice with different flip angles for said first spin species and said second spin species due to said frequency shift, and applying said excitation pulse with a disappearing flip angle for said second spin species; and a computerized processor configured to process the acquired magnetic resonance data to generate an electronic signal having a format from which a magnetic resonance image of said slice can be generated, said magnetic resonance image comprising substantially only signal contributions that originate from said first spin species, and to make said electronic signal available at an output of said processor.

20. A magnetic resonance apparatus configured to acquire magnetic resonance data from nuclear spins in a slice of an examination subject, said slice comprising nuclear spins of a first spin species and a second spin species exhibiting a frequency shift relative to each other and having respectively different spin-lattice relaxation times, said apparatus comprising:

a magnetic resonance data acquisition unit;

a control unit configured to operate said magnetic resonance data acquisition unit with the examination subject situated therein, to apply an inversion pulse that acts on a longitudinal magnetization of said first spin species in said slice and on a longitudinal magnetization of said second spin species in said slice;

said control unit being configured after a predetermined time period that is dependent on said spin-lattice relaxation time of said second spin species, to operate said magnetic resonance data acquisition unit to apply an excitation pulse and an associated first gradient pulse, that produce a transverse magnetization of said nuclear spins in said slice;

said control unit being configured after applying said excitation pulse and said associated first gradient pulse, to operate said magnetic resonance data acquisition unit to apply at least one manipulation pulse and an associated second gradient pulse, that produce at least one echo of said transverse magnetization of at least said first spin species, said second gradient pulse having an amplitude that is different from an amplitude of said first gradient pulse;

said control unit being configured to operate said magnetic resonance data acquisition unit to acquire magnetic resonance data from an entirety of said slice during said at least one echo;

said control unit being configured to operate said magnetic resonance data acquisition unit to suppress signals from said second spin species in the acquired magnetic resonance data by, applying said inversion pulse with a spatial domain profile of a flip angle thereof for said first spin species that is asymmetrical relative to a middle of said slice; and a computerized processor configured to process the acquired magnetic resonance data to generate an electronic signal having a format from which a magnetic resonance image of said slice can be generated, said magnetic resonance image comprising substantially only signal contributions that originate from said first spin species, and to make said electronic signal available at an output of said processor.

21. A magnetic resonance data apparatus configured to acquire magnetic resonance data from nuclear spins in a slice of an examination subject, said slice comprising nuclear spins of a first spin species and a second spin species exhibiting a frequency shift relative to each other and having respectively different spin-lattice relaxation times, said apparatus comprising:

a magnetic resonance data acquisition unit;

a control unit configured to operate said magnetic resonance data acquisition unit with the examination subject situated therein, to apply an inversion pulse that acts on a longitudinal magnetization of said first spin species in said slice and on a longitudinal magnetization of said second spin species in said slice;

said control unit being configured after a predetermined time period that is dependent on said spin-lattice relaxation time of said second spin species, to operate said magnetic resonance data acquisition unit to apply an excitation pulse and an associated first gradient pulse, that produce a transverse magnetization of said nuclear spins in said slice;

said control unit being configured after applying said excitation pulse and said associated first gradient pulse, to operate said magnetic resonance data acquisition unit to apply at least two manipulation pulses each with an associated second gradient pulse, that produce at least one echo of said transverse magnetization of at least said first spin species, each second gradient pulse having an amplitude that is different from an amplitude of said first gradient pulse;

said control unit being configured to operate said magnetic resonance data acquisition unit to acquire magnetic resonance data from an entirety of said slice during said at least one echo;

said control unit being configured to operate said magnetic resonance data acquisition unit to suppress signals from said second spin species in the acquired magnetic resonance data by applying said inversion pulse with a spatial domain profile of a flip angle thereof for said second spin species that, in an edge region of said slice, has an edge or a disappearing flip angle, and applying said excitation pulse with finite flip angles for said second spin species, and applying at least one of said at least two manipulation pulses, and said excitation pulse, with a spatial domain profile of the respective flip angles thereof having an edge; and a computerized processor configured to process the acquired magnetic resonance data to generate an electronic signal having a format from which a magnetic resonance image of said slice can be generated, said magnetic resonance image comprising substantially only signal contributions that originate from said first spin species, and to make said electronic signal available at an output of said processor.

22. A magnetic resonance apparatus configured to acquire magnetic resonance data from nuclear spins in a slice of an examination subject, said slice comprising nuclear spins of a first spin species and a second spin species exhibiting a frequency shift relative to each other and having respectively different spin-lattice relaxation times, said apparatus comprising:

a magnetic resonance data acquisition unit;

a control unit configured to operate said magnetic resonance data acquisition unit with the examination subject situated therein, to apply an inversion pulse that acts on a longitudinal magnetization of said first spin species in said slice and on a longitudinal magnetization of said second spin species in said slice;

said control unit being configured after a predetermined time period that is dependent on said spin-lattice relaxation time of said second spin species, to operate said magnetic resonance data acquisition unit to apply an excitation pulse and an associated first gradient pulse, that produce a transverse magnetization of said nuclear spins in said slice;

said control unit being configured after applying said excitation pulse and said associated first gradient pulse, to operate said magnetic resonance data acquisition unit to apply at least one manipulation pulse and an associated second gradient pulse, that produce at least one echo of said transverse magnetization of at least said first spin species, said second gradient pulse having an amplitude that is different from an amplitude of said first gradient pulse;

said control unit being configured to operate said magnetic resonance data acquisition unit to acquire magnetic resonance data from an entirety of said slice during said at least one echo;

said control unit being configured to operate said magnetic resonance data acquisition unit to suppress signals from said second spin species in the acquired magnetic resonance data by, applying said inversion pulse with a spatial domain profile of the flip angle thereof for said second spin species that, in an edge region of said slice, has an edge or a disappearing flip angle, and applying said excitation pulse with a disappearing flip angle for said second spin species; and a computerized processor configured to process the acquired magnetic resonance data to generate an electronic signal having a format from which a magnetic resonance image of said slice can be generated, said magnetic resonance image comprising substantially only signal contributions that originate from said first spin species, and to make said electronic signal available at an output of said processor.

23. A magnetic resonance apparatus configured to acquire magnetic resonance data from nuclear spins in a slice of an examination subject, said slice comprising nuclear spins of a first spin species and a second spin species exhibiting a frequency shift relative to each other and having respectively different spin-lattice relaxation times, said apparatus comprising:

a magnetic resonance data acquisition unit;

a control unit configured to operate said magnetic resonance data acquisition unit with the examination subject situated therein, to apply an inversion pulse that acts on a longitudinal magnetization of said first spin species in said slice and on a longitudinal magnetization of said second spin species in said slice;

said control unit being configured after a predetermined time period that is dependent on said spin-lattice relaxation time of said second spin species, to operate said magnetic resonance data acquisition unit to apply an excitation pulse and an associated first gradient pulse, that produce a transverse magnetization of said nuclear spins in said slice;

said control unit being configured after applying said excitation pulse and said associated first gradient pulse, to operate said magnetic resonance data acquisition unit to apply at least one manipulation pulse and an associated second gradient pulse, that produce at least one echo of said transverse magnetization of at least said first spin species, said second gradient pulse having an amplitude that is different from an amplitude of said first gradient pulse;

said control unit being configured to operate said magnetic resonance data acquisition unit to acquire magnetic resonance data from an entirety of said slice during said at least one echo;

said control unit being configured to operate said magnetic resonance data acquisition unit to suppress signals from said second spin species in the acquired magnetic resonance data by, applying said inversion pulse with a spatial domain profile of the flip angle thereof for said second spin species that has a maximized flip angle in a region in which said excitation pulse has finite flip angles for said second spin species, and applying said inversion pulse with a spatial domain profile of the flip angle thereof for said first spin species that is asymmetrical relative to a middle of said slice; and a computerized processor configured to process the acquired magnetic resonance data to generate an electronic signal having a format from which a magnetic resonance image of said slice can be generated, said magnetic resonance image comprising substantially only signal contributions that originate from said first spin species, and to make said electronic signal available at an output of said processor.

* * * * *